United States Patent [19]
Bujarski et al.

[11] Patent Number: 5,877,401
[45] Date of Patent: Mar. 2, 1999

[54] TARGETING AND ENHANCING RNA-RNA RECOMBINATION

[75] Inventors: Jozef J. Bujarski; Peter D. Nagy, both of DeKalb, Ill.

[73] Assignee: Board of Regents for Northern Illinois University, DeKalb, Ill.

[21] Appl. No.: 89,974

[22] Filed: Jul. 9, 1993

[51] Int. Cl.$^6$ .............................. A01H 5/00; C12N 15/82; C07H 21/02
[52] U.S. Cl. .................. 800/205; 435/172.3; 435/252.3; 435/320.1; 536/23.1; 536/25.1
[58] Field of Search .............................. 435/172.3, 320.1, 435/252.3, 410, 419; 800/205; 536/25.1, 23.1

[56] References Cited

PUBLICATIONS

Gal et al 1991 The EMBO Journal 10 (6):1571–1578.
Bujarski et al. 1986 Genetic recombination between RNA components of a multipartite plant virus, Nature, vol. 321, pp. 528–531.
Nagy et al 1992 (Nov.) Genetic Recombination in Brome Mosaic Virus, Journal of Virology, vol. 66, pp. 6824–6828.
Bujarski et al 1991 Generation and Analysis of Nonhomologous RNA–RNA Recombianants,Journal of Virology,vol. 65,pp.4153–4159.
Bujarski et al Modulation of replication, aminoacylation and adenylation *in vitro*, The EMBO Journal,vol.5, No.8, 1986, pp.1769–1774.

*Primary Examiner*—Douglas W. Robinson
*Assistant Examiner*—Elizabeth F. McElwain
*Attorney, Agent, or Firm*—Grace J. Fishel

[57] ABSTRACT

A construct formed from a first RNA molecule carrying an antisense insert complementary to a nucleotide sequence in a second target RNA molecule is used to direct crossovers between the first and second RNAs at or near the site of hybridization. The incidence of recombination and the location of recombinant junctions depends on the structure of the recombining RNA molecules and on the stability of the heteroduplex region. The RNA-RNA construct may be provided in double stranded DNA form. The DNA form may be inserted into a vector and used to transform or transfect a host.

28 Claims, 9 Drawing Sheets

TARGETING AND ENHANCING RNA-RNA RECOMBINATION

The invention was made in part with government funds under a grant from the U.S. National Institute for Allergy and Infectious Diseases (RO1 A126769). Therefore, the United States Government has certain rights in the invention.

BACKGROUND OF THE INVENTION

1. Field of the Invention

The present invention relates to methods and materials for targeting and enhancing RNA-RNA nonhomologous recombination by utilizing local complementarity between recombining RNA molecules.

2. Brief Description of the Prior Art

Genetic recombination in RNA viruses is defined as any process involving the exchange of information between genomic RNA molecules. RNA recombination is of interest for several reasons. First, it offers a means for manipulating RNA genomes (including genetic mapping). Second, the ability to exchange genetic information may confer a selective advantage on the virus and thus be a significant factor in its evolution (1, 2).

Recombination processes, as defined above, are of two kinds: homologous and nonhomologous. In the former, the parent RNAs are related to each other and the location of the genetic crossover is the same in both sequences, so preserving any reading frame and producing a potentially functional recombinant molecule. In nonhomologous recombination neither of these restrictions applies.

We have studied recombination in brome mosaic virus (BMV) previously. Brome mosaic virus is a plant virus in which three species of genomic RNA have a similar, though not identical, sequence at the 3' end (3). RNA-RNA recombination in BMV was first demonstrated after coinoculation with a mixture of wild-type (wt) RNA1, wt RNA2, and a mutated RNA3 (designated M4). M4 contained a short deletion in the 3' noncoding sequence (4). The repaired RNA3 progeny resulted from crossovers between M4 RNA3 and either RNA1 or RNA2. In a majority of recombinants, the crosses occurred at homologous (legitimate) positions, while some contained duplications of 3' noncoding sequences. Characterization of a large number of recombinants suggested that BMV RNAs can form local heteroduplexes at the crossover sites (5, 6).

In addition to two bromoviruses, BMV and cowpea chlorotic mottle virus (CCMV) (7–10), RNA-RNA recombination has been demonstrated experimentally in other plant viruses (11, 12), in animal viruses (13–17), and in bacteriophages (18, 19). As in BMV, formation of local heteroduplexes was proposed to promote RNA-RNA recombination in poliovirus RNAs (14) or to be involved in generation of poliovirus defective interfering RNAs (15). Using poliovirus mutants to inhibit the replication of one parent, Kirkegaard and Baltimore (13) showed that recombination occurs via a copy-choice mechanism. In Sindbis virus, mutated RNAs induced illegitimate recombinants that contained both viral and non-viral insertions (17), most likely via a mechanism analogous to that observed in bromoviruses.

A discontinuous copy-choice mechanism has been proposed for recombination between genomic, defective interfering, and satellite RNAs of turnip crinkle virus (11, 20). The acceptor crossover sites appeared to corresponding to the recognition sequences of the turnip crinkle virus RNA replicase. Some form of discontinuous recombination mechanism also has been postulated for mouse hepatitis coronavirus (16). The crossover hotspots resulted from selection rather than from specific sequences (21), suggesting a random nature of recombination for mouse hepatitis coronavirus.

In the present invention, experimental evidence is provided for hybridization-mediated recombination in single stranded viruses. A construct formed from a first RNA molecule carrying an antisense insert complementary to a nucleotide sequence in a second target RNA molecule is used to direct crossovers between the first and second RNAs at or near the site of hybridization. The incidence of recombination and the location of recombinant junctions depends on the structure of the recombining RNA molecules and on the stability of the heteroduplex region.

SUMMARY OF THE INVENTION

In view of the above, it is an object of the present invention to provide methods and materials for targeting the site of RNA-RNA nonhomologous recombination. It is another object to provide methods and materials that improve recombination efficiency. Other objects and features of the invention will be in part apparent and in part pointed hereinafter.

In accordance with the present invention, an RNA-RNA construct is prepared. The construct comprises a first RNA molecule derived from a single stranded RNA virus with an antisense insert complementary to a sequence in a second target RNA molecule. The first RNA molecule must be capable of initiating replication. The second target RNA molecule is also derived from a single stranded RNA virus. The first RNA molecule hybridizes with the second RNA molecule along the insert to form a heteroduplex. The heteroduplex directs the site of recombination and enhances the efficiency of recombination when the first RNA molecule is replicated in the presence of the second RNA molecule.

The RNA-RNA construct may be provided in double stranded DNA form. The DNA form may be inserted into a vector and used to transform or transfect a host. Recombination events will occur in the presence of the second RNA when the first RNA is transcribed, provided that the first RNA includes regions for binding RNA replicase necessary for initiating replication.

The invention summarized above comprises the methods and materials hereinafter described, the scope of the invention being indicated by the subjoined claims.

DESCRIPTION OF THE DRAWINGS

In the accompanying drawings, in which several of various possible embodiments of the invention are illustrated, FIG. 1 (Upper) is a schematic representation of the 3' terminal noncoding regions in the wt BMV RNA1 and in mutated BMV RNA3 constructs. The RNA3 mutants [PN1 (−) through PN10(−)] are all derivatives of PN0 RNA3, which has a mutated 3' noncoding region with sequence duplication (described in ref. 6). In addition to the above duplication, the 3' noncoding region of PN0 contains a 196-nt 3' noncoding sequence of CCMV RNA3 (stippled box). The location of primers used for reverse transcription-polymerase chain reaction (RT-PCR) analysis (see FIG. 2B) is shown by short horizontal arrows above the PN0 construct. X, S, K, and E mark the positions of Xba I, Spe I, Kpn I and EcoRI restriction sites, respectively. For estimation of the total length of the 3' noncoding region, see scale at the top. Coding regions, an intercistronic RNA3 region, and 5' noncoding regions (not to scale) are represented by solid boxes, a short horizontal line, and open boxes, respectively. The location of RNA1 sequences used as inserts is marked by a horizontal arrow below the RNA1 molecule (the head of the arrow shows the sense orientation). (Lower) PN1(−) through PN10(−) were obtained by ligation of RNA1-specific cDNA sequences (represented by solid horizontal arrows) into PN0 at the Spe I site. The sense or antisense orientations of the inserts are shown by the heads of the arrows. The dotted region on the left side of the PN6(−) arrow depicts the area of C→U mutations, and one or three small curves in PN7(−) to PN10(−) arrows represent mismatch mutations. PN2(−)NR is a derivative of the PN2(−) that does not contain the 3' terminal 46-nt promoter sequence and therefore did not replicate. Please refer to FIGS. 3A–3E for sequence details. The number of lesions examined as well as the recombination incidence (defined as the percentage of local lesions on C. quinoa leaves that accumulated recombinants) are shown on the right.

(FIG. 2A) Northern blot analysis of BMV RNA components in total RNAs isolated from local lesions of C. quinoa. Progeny RNAs of PN0 lesions 1–5), PN2(+) (lesions 6–11), and PN2(−) (lesions 12–18) were probed with antisense $^{32}$P-labeled RNA transcripts representing the last 200 nt conserved BMV RNA region. Lanes Φ, parental mutant RNA3 transcripts. The position of individual BMV RNA components is shown on the left, and the migration of parental RNA3 transcripts and the progeny recombinants is depicted by the letters T and R, respectively, on the right.

FIG. 2B Electrophoretic analysis of RNA3-specific cDNA obtained by RT-PCR using primers 1 and 2 to amplify of the total RNA preparations analyzed in FIG. 2A. Control RT-PCR amplifications (lanes Φ) were performed with mixtures of in vitro transcribed wt BMV RNA1 and RNA2 and the mutated RNA3 components. The position of PCR products corresponding to the expected length of the parental (inoculated) RNA3 mutants is indicated on the left (T), whereas that for newly emerged recombinants is indicated on the right (R). A standard 1-kb DNA ladder (GIBCO/BRL) is shown in lanes 1 KB. Faster-migrating low-intensity bands (S) correspond to artifactual cDNA products that emerged due to weak priming at the boundary of the duplicated 3' region (see FIG. 1).

DETAILED DESCRIPTION OF THE INVENTION

Figure 1:
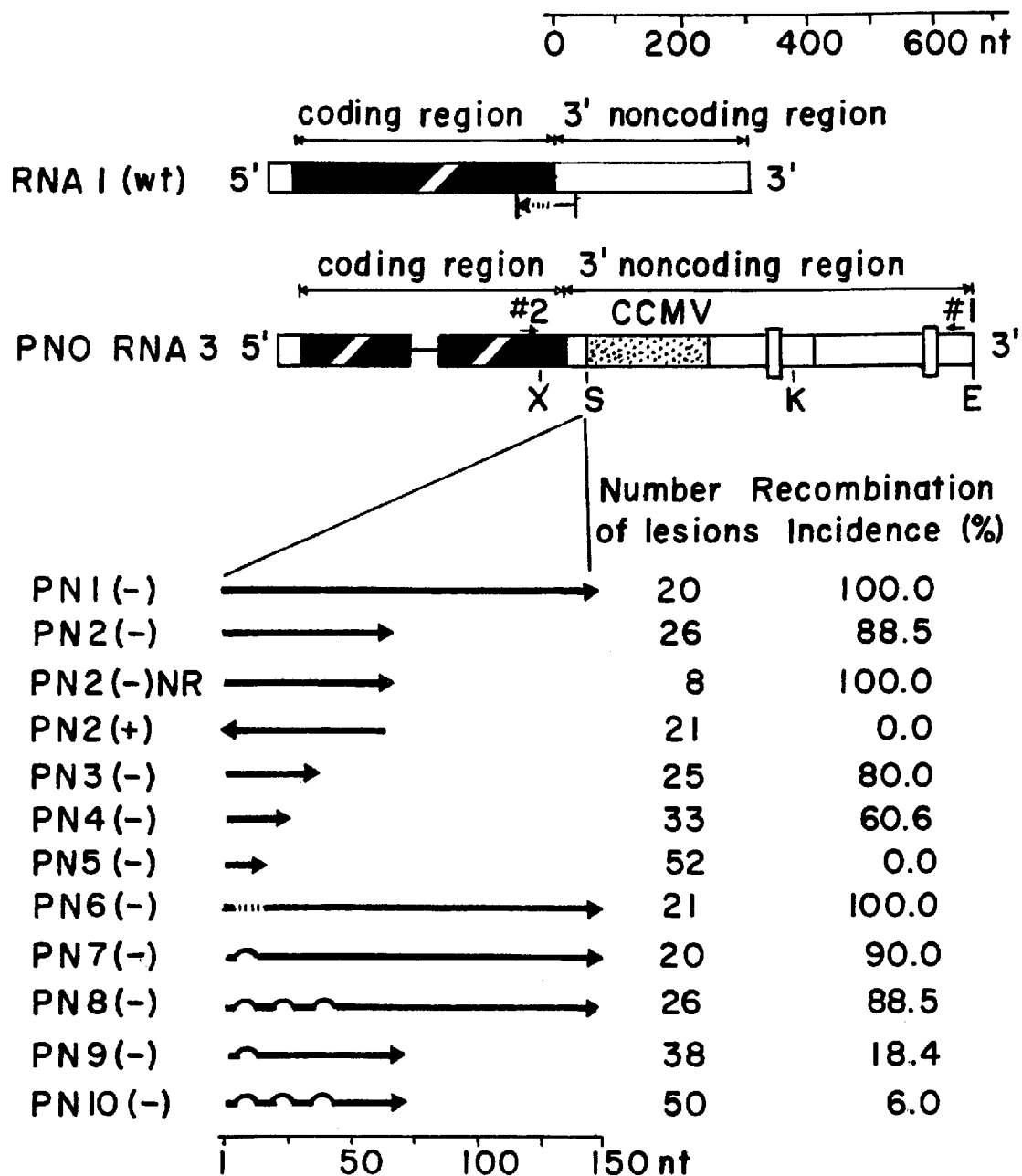

The site of RNA-RNA nonhomologous recombination can be directed and the efficiency of recombination improved when a first RNA molecule has an antisense insert which is complementary to a target nucleotide sequence in a second RNA molecule. When the RNA molecules are brought together, they hybridize along the antisense insert and form a heteroduplex. During replication, the heteroduplex directs the site of recombination and enhances the efficiency of recombination. For this to occur, the first RNA molecule must be capable of initiating replication.

The antisense insert may be complementary to a sequence in a noncoding region of the target RNA molecule, to a region between reading frames or even to a sequence in a reading frame, if the reading frame is restored by recombination or if the sequence is not essential. The antisense insert must be long enough so that the area of complementarity forms a stable heteroduplex.

The invention as described above has been demonstrated effective with RNA molecules derived from brome mosaic virus (BMV). BMV is a member of the bromoviruses group which includes broad bean mottle virus (BBMV) and cowpea chlorotic mottle virus (CCMV) and is part of the Sindbis superfamily of viruses. It is believed that the invention is useful, in general, with single-stranded, viral RNA molecules of plant or animal derivation.

A majority of the recombinants formed during replication have crossovers juxtaposed at or near counterpart nucleotides in the heteroduplex region but in other recombinants, the donor and acceptor sites may be more widely spaced. The acceptor sites may be affected by secondary structure on either side of the insert and by nucleotide mismatches which destabilize the heteroduplex. In the case of BMV when the mismatches are on the upstream side of the antisense insert, the acceptor sites are shifted towards the middle of the heteroduplexed region. Downstream mismatches have less effect. Comparable findings are expected with RNA molecules having similarly featured replicases because replicase is believed to be the driving force behind recombination.

An RNA-RNA recombination construct useful in directing the site of recombination is formed by ligating an antisense insert into a first RNA molecule. The first RNA molecule must be capable of initiating replication. The antisense insert is engineered such that it has a nucleotide sequence that is complementary to a target sequence in a second RNA molecule. The sequence must be long enough such that a stable heteroduplex will form along the region of complementary. For this purpose, it is believed that the nucleotide sequence should be at least 25 nucleotides long. With BMV, satisfactory results have been obtained when the complementary region of the insert was between about 40 and about 100 nucleotides long. Longer areas of complementarity may interfere with RNA replication processes.

A double stranded DNA which transcribes the RNA-RNA construct is obtained by cDNA synthesis or by purification and isolation from native genetic material. The double stranded DNA is inserted into a vector for transforming or transfecting a prokaryotic or eukaryotic host. Suitable vectors are plasmids and may also include viruses and so forth. To be expressed in the host, the DNA sequence must be operably linked to a promoter that is functional in at least some of the host cells into which the vector is introduced. In the presence of a second RNA molecule having the target sequence, recombination events will occur when the DNA sequence is expressed provided that the first molecule initiates replication. Some replicatable recombinants may be of interest.

The following nonlimiting examples illustrate the invention:

EXAMPLE 1

Materials and Methods (1) Materials. Plasmids pB1TP3, pB2TP5, pB3TP7 and pCC3TP4 (a generous gift of Paul Ahlquist, University of Wisconsin, Madison)—containing full-length cDNA copies of wt BMV RNA components 1, 2 and 3 and CCMV RNA3, respectively—were used to synthesize infectious viral RNA transcripts (22, 23). The following primers were used in this study (the mutated sequences are under lined): 1, CAGTGAATTCTGGTCTCTTTTAGAGATTTACAG SEQ ID NO:23; 2, CTGAAGCAGTGCCTGCTAAGGCGGTC SEQ ID NO:24; 3, CAGTGAATTCTTTCGACTAGGCGCTGCCCACCA SEQ ID NO:25; 4, CAGTACTAGTTTAAGTGATGCGCTTGTCTC SEQ ID NO:26; 5, CAGTACTAGTCGCTTGTCTCTGTGTGAGACC SEQ ID NO:27; 6,CAGTACTAGTTGTGTGAGACCTCTGCTCGA SEQ ID NO:28; 7, TAGTCTCGAGCAGAGGTTTTATATAGAGACAAGCGCATCA SEQ ID NO:29; 8, CTAGTCTCGAGGTCTCACAGGATCCAGACAAGCGCATCACTTAACAC SEQ ID NO:30; 9, ACAGGATCCAGACAAGCGACGCGTACTTAACACGCTAGCTAAAGATCAAATCACCAG SEQ ID NO:31.

(2) Plasmid construction. The PNx plasmids (described below) are derivatives of pB3TP7, from which infectious BMV RNA3 can be synthesized in vitro (22). To construct PN0 (FIG. 1), PCR mutagenesis (24) with primers 2 and 3 was used to place a 196-bp fragment of pCC3TP4 (positions 1954–2150; ref. 23) into a pB4DM4 construct (6) between Ban II and HindIII restriction sites.

To generate PN1(−), a Dra I-Xho I fragment of pB1TP3 (positions 243–382, counted from the 3' end) was blunt-end ligated into PN0 at the unique Spe I site (FIG. 1). The constructs PN2(−) and PN2(+) were obtained in the same way as PN1(−) except that the Sac I-Xho I fragment of pB1TP3 (positions 243–308) was inserted in antisense and sense orientations, respectively. PN2(−)NR was generated by digestion of PN2(−) with Kpn I and EcoRI (FIG. 1), treatment with T4 DNA polymerase, addition of EcoRI linkers, and religation of the desired fragment isolated by agarose electrophoresis.

Three PN2(−) derivatives [PN3(−), PN4(−) and PN5(−)] were obtained by deleting downstream portions of the PN2(−) antisense region. Portions of PN2(−), that included a short upstream 3' noncoding sequence and various parts of the antisense region were amplified by PCR using primer 2 in conjunction with primers 4, 5 and 6 for construction of PN3(−), PN4(−) and PN5(−), respectively (FIG. 1). The PCR products were digested with Spe I (partially) and Xba I and then ligated into PN0 between the Spe I and Xba I sites.

To generate PN6(−) and PN7(−), the 3' noncoding region of PN1(−) was amplified by using primer 1 and either primer 7 or 8. The PCR products were digested with Xho I and EcoRI and ligated between these sites in PN2(−) (FIG. 1). Primer 7 replaced four cytosine residues with four thymine residues. Primer 8 deleted five nucleotides in the upstream part of the PN1(−) antisense region. In addition, it introduced a unique BamHI site several bases downstream of the above deletion (see FIGS. 3A–3E). PN9(−) was constructed in the same way as PN7(−), but PN2(−) was the template used for PCR. Parts of the 3' noncoding region of PN7(−) and PN9(−), respectively, were reamplified by PCR using primers 1 and 9, to construct PN8(−) and PN10(−) (FIG. 1). The PCR products were digested with BamHI and EcoRI and ligated into PN7(−) that was linearized with the same enzymes. Primer 9 replaced three and four bases with size-base heterologous sequences at two locations in the antisense region of PN7(−) and PN9(−). Sequencing confirmed all the above modifications.

3. Plant Inoculations. *Chenopodium quinoa,* a local-lesion host, was inoculated with a mixture of 1 $\mu$g of each of the following transcribed RNAs: wt RNA1, wt RNA2, and one of the mutated PNx RNA3 molecules, as described (6). The accumulation of recombinant RNA was analyzed by Northern blot hybridization (6).

4. Cloning and Sequencing of Recombinants. Total nucleic acids were extracted from individual lesions and the 3' end of the progeny RNA3 species was amplified as described (6), by RT-PCR with primers 1 and 2. The resulting cDNA products were digested with an EcoRI/Xba I mixture and ligated between these sites in the PGEM-3'Zf (−) cloning vector (Promega). Junction sites were determined by sequencing.

5. Results: Local Complementarity Between BMV RNAs Directs Crossovers. The proposed role of local heteroduplexes in recombination was tested by generating BMV RNA3 molecules that contained a 66-nt insert complementary to wt RNA1 in the upstream part of the mutated 3' noncoding region (FIG. 1). This RNA3 mutant [designated PN2(−)] was coinoculated with wt RNA1 and wt RNA2 transcripts on leaves of *C. quinoa,* a local-lesion BMV host. Northern blot analysis revealed the accumulation of novel RNA3 molecules that were smaller than PN2(−) RNA3 (FIG. 2A). Electrophoresis of RT-PCR-amplified cDNA products revealed size heterogeneity of the 3' noncoding RNA3 sequences among the recombinants present in separate local lesions (FIG. 2B). The five clones examined for each lesion had the same sequences in 90% of the cases (data not shown). This indicated that single types of recombinants predominated in most of the lesions. In 10% of the lesions two types of recombinants were found. Sometimes parental mutant RNA3 molecules coaccumulated with the progeny recombinants (as in lanes 13–15 of FIG. 2B).

Of 25 RNA3 recombinants isolated from local lesions, all contained RNA1 sequences that crossed within the sequence complementary of the 66-nt antisense PN2(−) region. The acceptor sites were located in or close to the 5' part of PN2(−) antisense region. Consequently, the RNA3 progeny contained almost the entire 3' noncoding region taken from RNA1, with the crossovers occurring at nonhomologous positions. Displayed on the putative heteroduplex formed between PN2(−) RNA3 and wt RNA1, the acceptor and donor sites were clustered at or near the left side of the duplex (FIGS. 3A–3E).

To demonstrate that recombination activity of PN2(−) depended on its antisense region, we tested the in vivo stability of two control constructs, PN0 and PN2(+). PN0 RNA3 contains the same 3' noncoding region as PN2(−) but without the antisense insert, and PN2(+) has the 66-nt RNA1-derived sequence in the sense orientation. Northern blot hybridization as well as RT-PCR analysis (FIGS. 2A and B, respectively) detected only parental PN0 or PN2(+) RNA3 progeny. Sequencing revealed no recombination or sequence rearrangements among the cloned RT-PCR products. PN2(+) was prepared for purposes of comparison and is not a construct in accordance with the present invention.

Figure 2A:
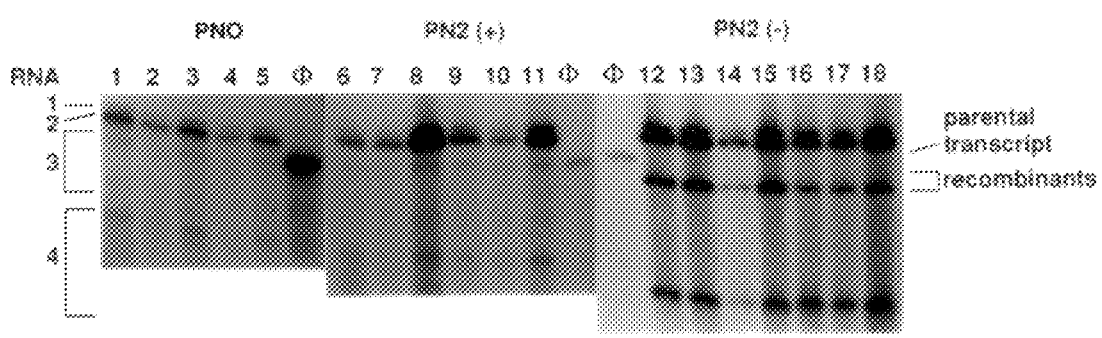
FIGS. 2A and 2B are a characterization of BMV RNA3 recombinants.
Figure 2B:
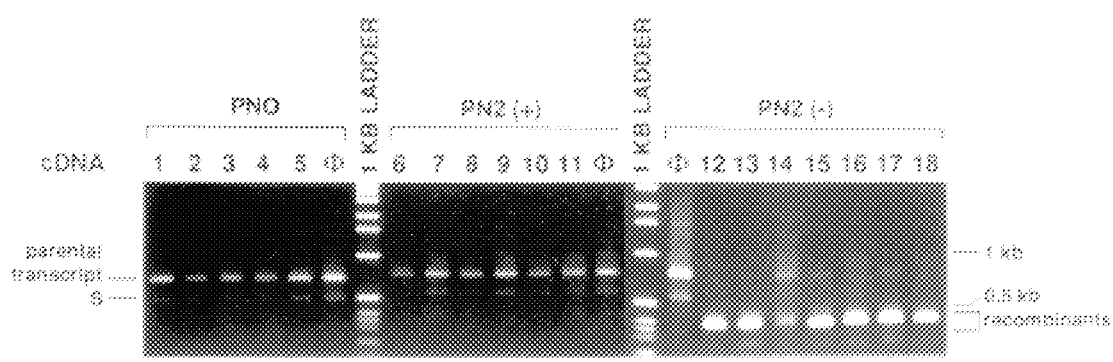
Figure 3A:
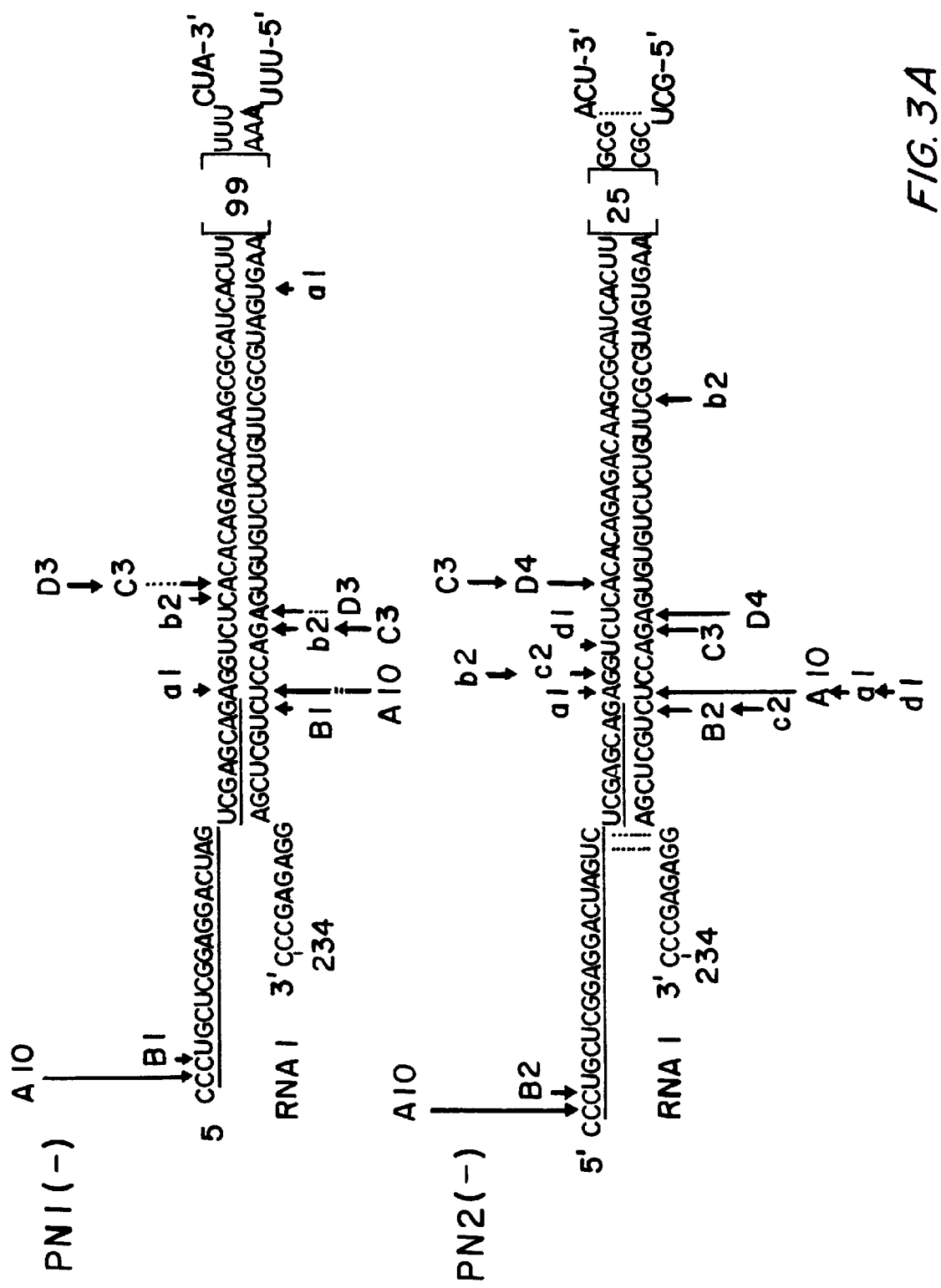
FIGS. 3A–3E shows the location of crossover sites in the recombinant BMV RNA3 molecules generated with PNx constructs: PN1(−) is a heteroduplex formed between SEQ ID NO:1 AND SEQ ID NO:2, PN2(−) is a heteroduplex formed between SEQ ID NO:3 and SEQ ID NO:4, PN3(−) is a heteroduplex formed between SEQ ID NO:5 and SEQ ID NO:6, PN4(−) is a heteroduplex formed between SEQ ID NO:7 and SEQ ID NO:8, PN5(−) is a heteroduplex formed between SEQ ID NO:9 and SEQ ID NO:10, PN6(−) is a heterduplex formed between SEQ ID NO:11 and SEQ ID NO:12, PN7(−) is a heteroduplex formed between SEQ ID NO:13 and SEQ ID NO:14, PN8(−) is a heterduplex formed between SEQ ID NO:15 and SEQ ID NO:16, PN9(−) is a heteroduplex formed between SEQ ID NO:17 and SEQ ID NO:18, PN10(−) is a heteroduplex formed between SEQ ID NO:19 and SEQ ID NO:20 and PN2(−)NR is a heteroduplex formed between SEQ ID NO:21 and SEQ ID NO:22. The antisense region of PNx (upper line, in 5'→3' direction) is shown hybridized to the complementary (sense) sequence of the 3' noncoding region of BMV RNA1 (lower line, in 3'→5' direction). The region of RNA3 that potentially could form a stem-and-loop structure (see below) is underlined. The nucleotide of the wt RNA1 part and the first nucleotide of a given PNx RNA3 part which are joined in the particular recombinant are depicted by arrows with the same letters on both RNA strands. The size of the arrow is proportional to the number of independent lesions (indicated also by the numbers at the letters) on C. quinoa that contained this particular recombinant. Uppercase letters mark those crossover sites that were generated by more than one PNx RNA3 construct, whereas lowercase letters (starting from letter "a" for each heteroduplex) show unique crossover sites. The C→U transitional mutations in PN6(−) are depicted by bold letters with asterisks. The amount of not-shown heteroduplex nucleotides is indicated by numbers in brackets. In addition to the sequences presented, in some lesions some recombinants had nontemplated extra nucleotides at the crossover sites, as follows (numbers in parentheses show the number of lesions that accumulated given recombinants): U in PN6(−)-c (1), PN6(−)-c (1), PN6(−)-E (2), and PN8(−)-c (1); UU in PN2(−)-a (1), PN6(−)-d (1), PN6(−)-c (1), and PN6(−)-F (1); UA in PN2(−)-d (1); UUU in PN1(−)-B(1).
Figure 3B:
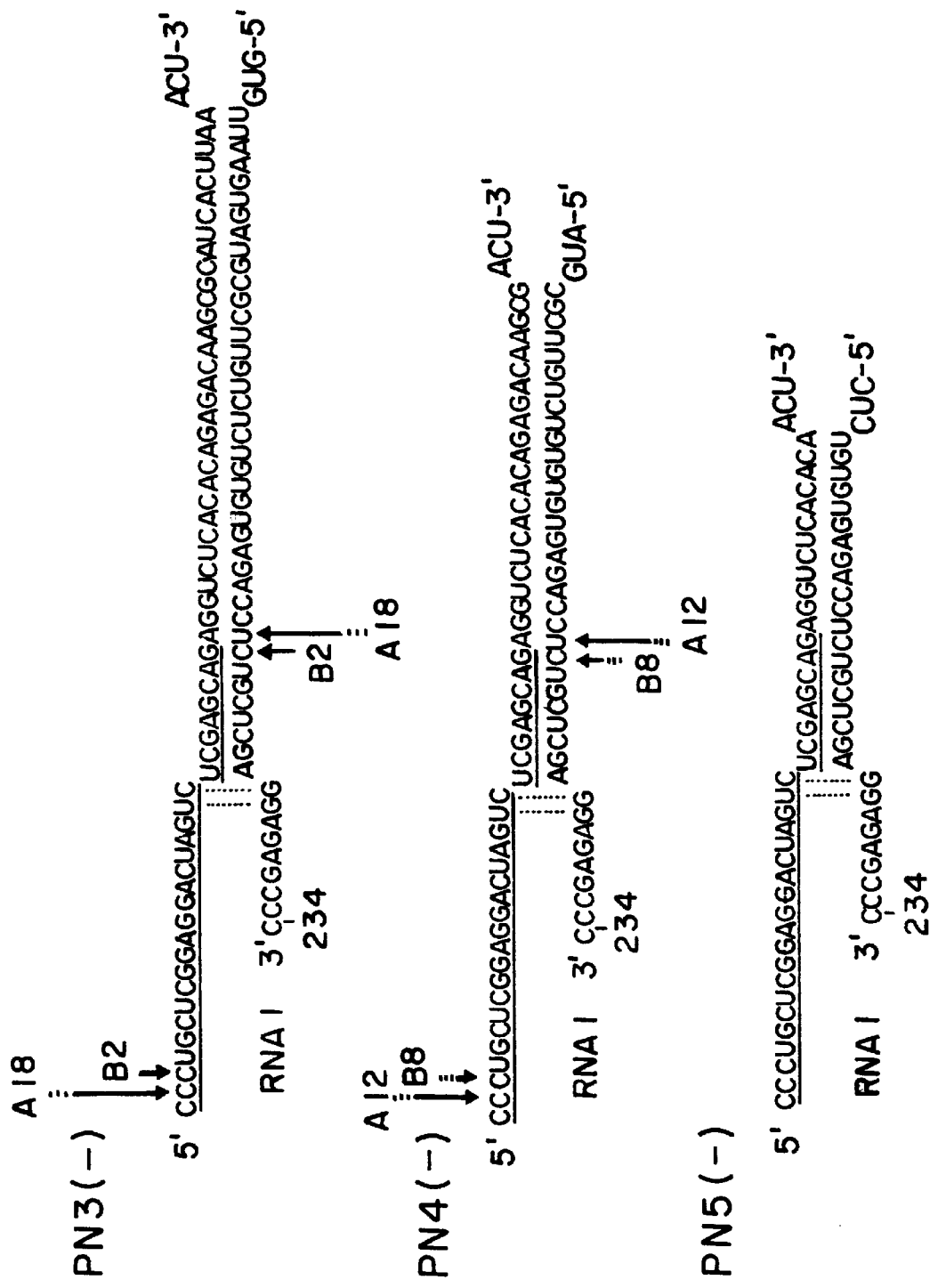
Figure 3C:
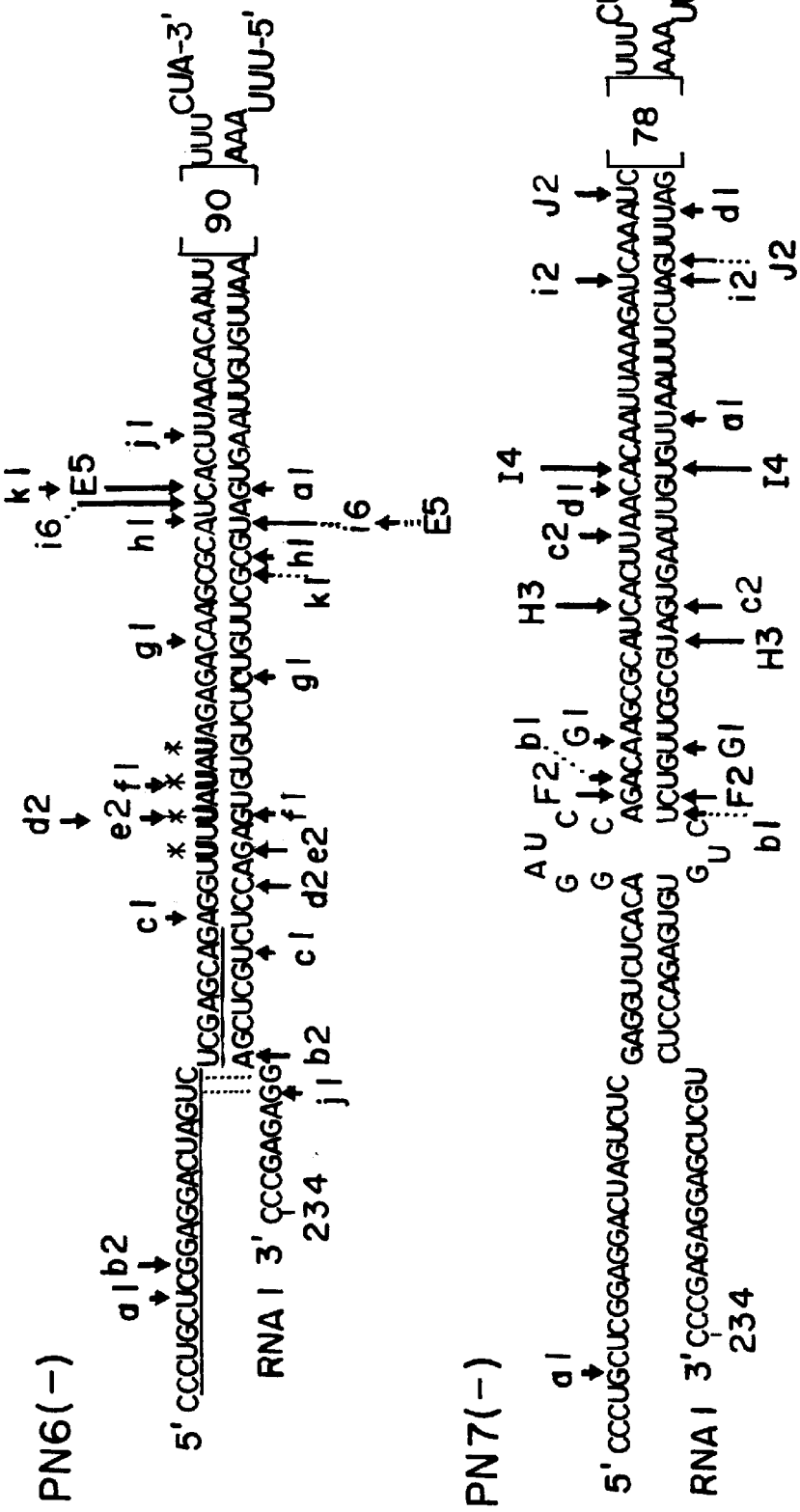
Figure 3D:
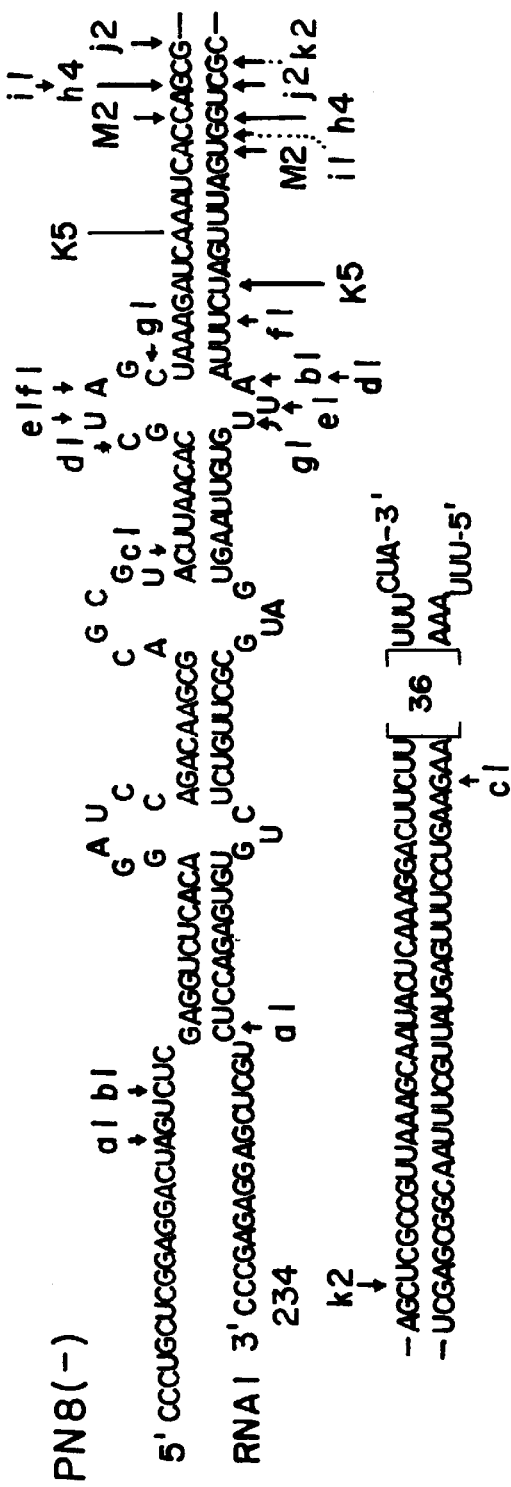
Figure 3D:
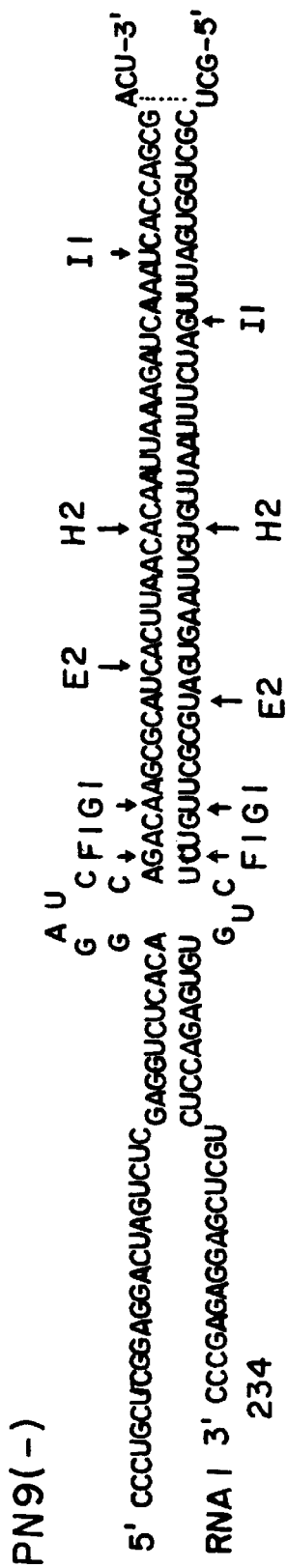
Figure 3E:
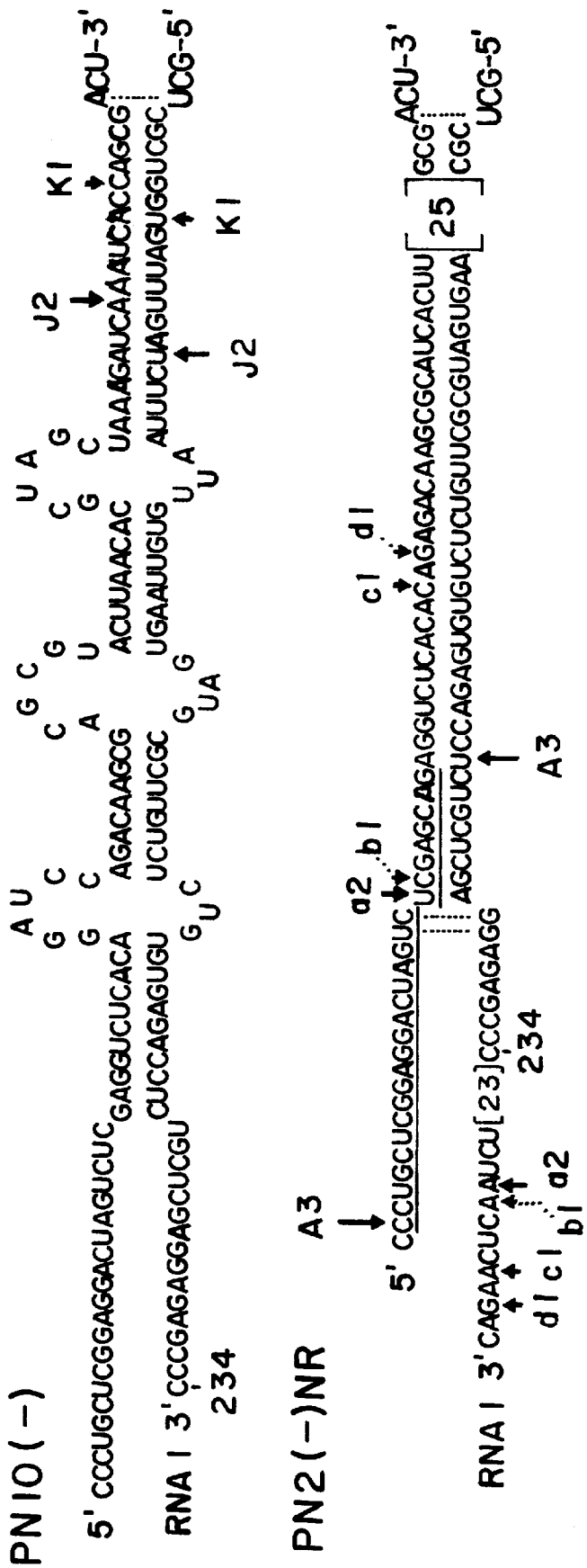

A selective amplification of the parental RNA3 sequences from a mixture of transcribed mutated RNA3 controls with wt RNA1 and RNA2 allowed us to rule out the possibility that these recombinants were generated by RT-PCR itself. No recombinants were observed (FIG. 2B, lanes Φ). Moreover, the recombinant RNA3 molecules accumulated to high levels within the lesions (FIG. 2A).

Ton confirm the formation of stable heteroduplexes between PN2(−) RNA3 and RNA1, we performed an in vitro RNase-protection analysis. RNase-resistant RNA1 fragments of the expected size were obtained after hybridization of nondenatured PN2(−) RNA3 and $^{32}$P-labeled wt RNA1 (data not shown). The control reactions with either PN0 or PN2(+) RNA3 did not generate any specific RNase-resistant fragments.

6. Effect of Modifications in the Antisense Inserts on the Incidence of Recombination and on Crossover Location. To further test the role of antisense inserts in targeting nonhomologous recombination, we determined the effect of the length of the complementary sequence. PN1(−) contained the same 66-bp antisense insert as PN2(−) plus an additional 74-bp inverted RNA1 cDNA sequence (nt 243–382 of RNA1, counted from the 3' end). Plasmids PN3(−), PN4(−) and PN5(−) contained 40-, 30- and 20-bp antisense RNA1 cDNA fragments nested at a common RNA1 position, nt 243. Sequencing of cloned, RT-PCR-amplified cDNA products revealed than transcribed PN1(−), PN3(−) and PN4(−), but not PN5(−), generated recombinant RNA3 progeny in *C. quinoa* (FIG. 1). This suggested that an antisense sequence longer than 20 nt is necessary to promote efficient recombination. PN5(−) is not in accordance with the present invention.

The incidence of recombination depended on the length of the antisense sequence (See FIG. 1). The acceptor sites in recombinants obtained with PN1(−) through PN4(−) transcripts clustered within or close to the upstream part of the antisense sequence on RNA3 (FIGS. 3A–3E). The donor sites clustered within the complementary region of RNA1. All the crossovers were found at or near the left side of the putative heteroduplex (FIGS. 3A–3E). The lack of recombination in PN5(−) infections indicated, however, that the central and right-side parts of the duplex were also important in recombination, possibly by stabilizing the active left side.

An alternative explanation of the recombination hotspots found in PN1(−) through PN4(−) recombinants is that they might result from selection for viable recombinants. To test the role of selection in recombination, sequence alterations were introduced outside the hotspot sequences observed for PN1(−) through PN4(−) recombinants. The PN6(−) construct allowed for the formation of four weak G·U base pairs at the left side of the putative PN6(−)-RNA1 heteroduplex. Although, compared with the PN1(−) mutant, this did not affect the incidence of recombination (FIG. 1), it shifted the crossover sites toward the central part of the duplex (FIGS. 3A–3E). This result confirmed the importance of the left-side portion in directing the site of recombination.

The above conclusion was supported by the results obtained with PN7(−) through PN10(−) constructs. Plasmid PN7(−) had a 5-nt deletion in the upstream part of the antisense region as compared to PN1(−). Also, further downstream, it contained a 6-nt heterologous sequence that disrupted the left side of the heteroduplex (FIGS. 1 and 3). As in PN6(−), the modification in PN7(−) occurred downstream to recombination hotspot regions of PN1(−)- through PN4(−)-derived recombinants. The acceptor sites in PN7 (−)-generated recombinants were shifted downstream on RNA3, while the donor sites were moved upstream on RNA1, compared with those of PN1(−) recombinants. Plasmid PN8(−) contained the same antisense sequence as PN7(−) with two additional downstream mismatch regions (FIG. 1). It generated recombinants with the acceptor and donor hotspots shifted into the central part of the antisense PN8(−) insert and into the RNA1-complementary region, respectively. Compared with PN1(−), the hotspots generated by PN8(−) were 31–84 nt downstream in the RNA3 antisense region and 31–59 nt upstream on RNA1. Consequently, the PN8(−)-generated recombinants had 30–50 and 50–150 more nucleotides in their 3' noncoding regions than those generated by PN7(−) and PN1(−), respectively. Thus, while the majority of PN1(−)-derived recombinants contained a shorter-than-wt 3' noncoding region, the PN8(−)-generated recombinants were ≈100 nt longer in this region. In total, the crossovers supported by PN1(−) through PN4(−) were not observed for PN7(−) and PN8(−), although they shared sequences found to be active in PN1(−) through PN4(−). This suggested that the crossovers were primarily determined by the structure of the heteroduplex rather than by selection (see Discussion).

Previously, we proposed that partial hybridizations occur between recombing BMV RNAs at the sites of crossovers (5, 6). Constructs PN9(−) and PN10(−) (FIG. 1) were designed to imitate such structures. They could potentially form much energetically weaker heteroduplexes with RNA1 than could PN1(1), PN2(−), PN7(−) or PN8(−). Indeed, PN9(−) and PN10(−) demonstrated a significantly reduced incidence of recombination. The location of recombinant crossovers was within sequences capable of heteroduplex formation (FIGS. 3A–3E).

To test whether the heteroduplex-driven crossovers could take place between the positive strands, PN2(−)NR, a non-replicating derivative of PN2(−) RNA3, was examined. PN2(−)NR lacked the last 46 nt of the 3' RNA replication promoter (25, 26).

Consequently, it did not produce a detectable amount of negative strands in barley protoplasts (not shown). All the lesions generated by PN2(−)NR contained RNA3 recombinants with the crossovers within or in close vicinity to the regions capable of hybridization with RNA1 (FIGS. 3A–3E). This suggested that recombination could occur between hybridized positive strands of PN2(−)NR and RNA1 (See discussion).

6. Discussion. Heteroduplex-Primed Nonhomologous Recombination. The results reported in this example provide experimental evidence that local complementarity between viral RNA molecules can promote recombination events. The formation of stable double-stranded regions between PNx(−) RNA3 and wt RNA1 molecules was confirmed in vitro by RNase protection experiments (data not shown). Constructs that lacked antisense sequences did not generate recombinants and did not form stable duplexes with RNA1 in vitro.

The heteroduplex-primed crossover events generated RNA3 recombinants that differed in size from wt and that had almost the entire 3' noncoding region replaced by that of the RNA1 segment. Because of that and because the crossovers occurred within nonconserved, upstream sequences of the 3' noncoding region, the recombinants described here can be defined as nonhomologous (illegitimate). Lai (27) differentiates between "regular" and "aberrant" homologous crossovers as those which occur between homologous sequences at symmetrical and asymmetrical locations, respectively. In our system, recombination is driven by sequence complementarity between the recombination substrates rather than by sequence homology. One can envision the involvement of heteroduplexes in homologous or aberrant homologous recombination if double-stranded regions were formed by palindromic sequences.

Effects of Heteroduplex Structure on Recombination in Hotspots and Mechanism of Recombination. It has been proposed for coronaviruses that recombination occurs randomly and that the recombination hotspots result from natural selection (26). However, these processes cannot account for the observed differences in the recombination activity of poorly replicating parental BMV PNx molecules. For instance, the fact that PN8(−) did not accumulate the same recombinant classes which PN1(−) and PN7(−) did, although the hotspot sequences of PN1(−) and of PN7(−) were available in PN8(−), strongly supports the important of hybridized (double-stranded) regions in recombination. Identification of a whole spectrum of RNA3 recombinants which contained 3' noncoding regions of variable length (between 231 and 403 nt) and a variety of sequences, demonstrated that different kinds of crossovers were selectionally permissible. Therefore, the contribution of selection factors for viable recombinants in the observed crossovers must be of limited importance.

The concentration of crossovers in recombinants generated by PN1(−) through PN4(−) was observed at the left side of the heteroduplex (FIGS. 3A–3E). This can be explained by assuming that the replicase complex did not unwind the double-stranded region efficiently and switched between the templates before penetrating further downstream. Such a template switching mechanism is supported by the observed shift of the crossovers toward central parts of the heteroduplex when hybridization at the left side was weakened or disrupted. This mechanism is also supported by the presence of nontemplated (mainly uracil residues; see the legend of FIGS. 3A–3E) nucleotides at the crossover sites. They were probably introduced by replicase stuttering during template switching. Similar results have been shown for recombination in turnip crinkle virus (11, 20).

According to an alternate breakage-and-religation mechanism, preferential cleavage and ligation near the ends of a stable duplex would also explain the concentration of crossovers at the terminal sides. In our system, however, this would be more probable at the right side of the duplex. Digestions at the left side would release the 5' RNA3 and the 3' RNA1 fragments, which would be free to dissociate in the absence of complementary sequences. Thus, although not definitely distinguishing between alternate mechanism of recombination, the observed location of crossovers at the left side is better explained by a template-switching mechanism.

A majority of recombinants had crossovers juxtaposed at or near counterpart nucleotides. Some recombinants, however, had the donor and acceptor crossing sites far apart from each other on or near the heteroduplex. Secondary structure elements were predicted to exist at some crossover sites on the mutated RNA3 molecules (see underlined regions in FIGS. 3A–3E). This may position the RNA1 and RNA3 sites closer to each other, thus allowing the viral replicase to switch templates at more-upstream RNA3 locations.

In the heteroduplex-mediated system, recombination could occur between either two negative or two positive strands, which could lead to similar recombinants. The recombination competence of a nonreplicating construct PN2(−)NR, as well as other previously reported BMV RNA mutants (8, 9) strongly suggests that the recombination events can occur between positive strands during negative-strand synthesis. Also hybridizations between positive strands are more likely than hybridizations between negative strands, simply because positive-stranded RNA is much more abundant than negative-stranded RNA in BMV infections (28).

EXAMPLE 2

In this example, a target (modified BMV RNA3 molecule) will be expressed as mRNA in transgenic plants whereas the acceptor (another modified BMV RNA3 molecule) will be inoculated on transgenic plants in a form of in vitro transcript (together with transcribed wt BMV RNAs 1 and 2). N. benthamiana plants will be used in this study because, unlike N. tabacum (tobacco) species, they can serve as efficient systemic hosts for BMV.

Figure 4:
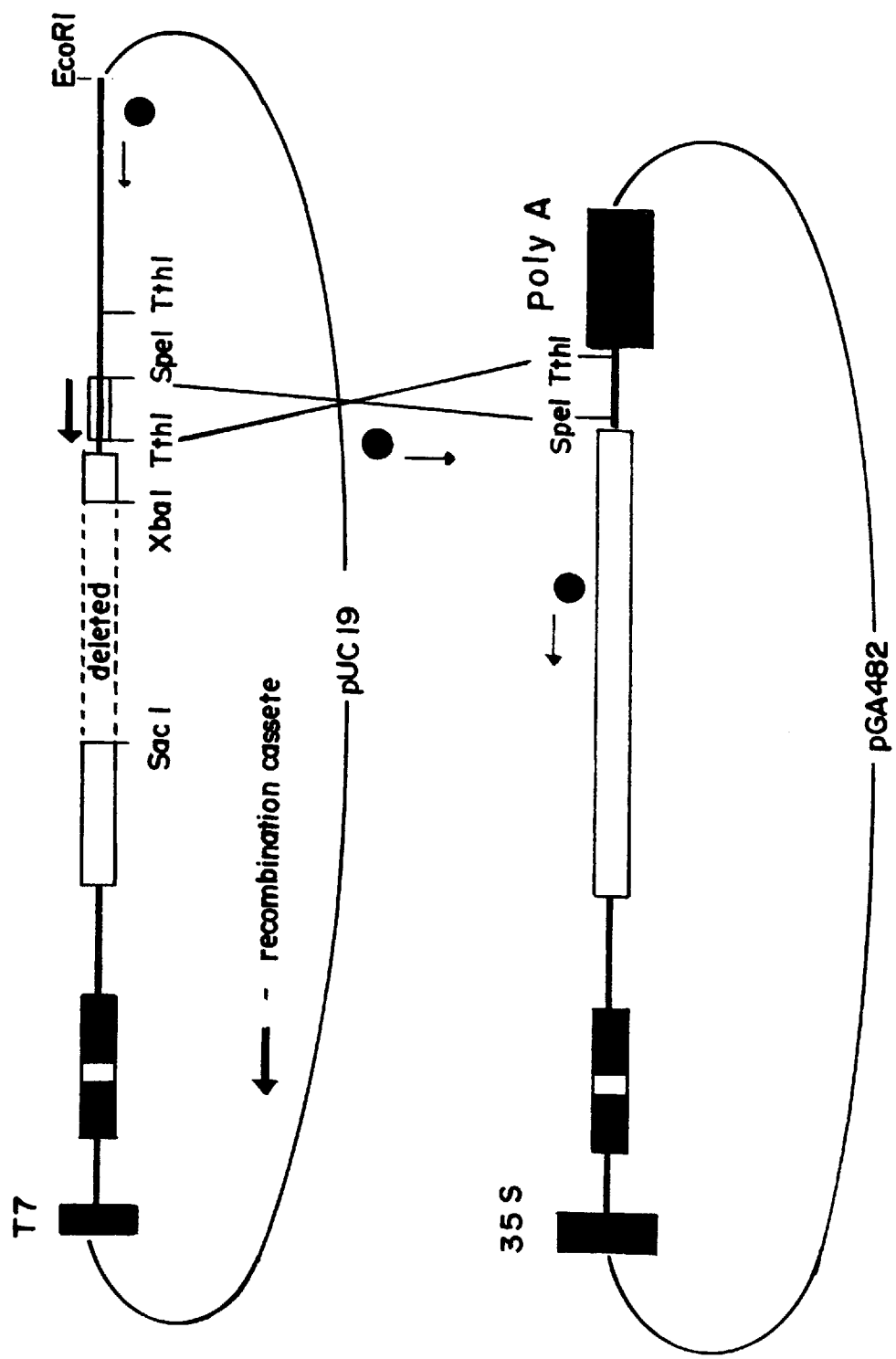
FIG. 4 shows one example of engineering of recombinationally-active BMV RNA3 molecules.

The recombinationally-active donor BMV RNA3 segment will be designed, as illustrated in FIG. 4A. This construct will have a 150 nt (between Spe I and TthI restriction sites) 3' noncoding region repeated and inserted in a reverse (antisense) orientation. This will introduce a recombination cassette capable of bringing the donor and target RNA molecules together due to local hybridization along the complementary region. This should direct the recombinant crosses to a region previously demonstrated to be active in recombination. In addition, the donor construct will have most of the coat protein ORF deleted in order to inactivate the virus. Previous studies demonstrated that BMV requires the CP molecule to assure systemic spread in N. benthamiana. The only way to restore the systemic infection would be by recombination with the target mRNA expressed in the transgenic plants (see below).

In addition to the above modifications, donor RNA will have a stable marker mutation in order to guard against a possibility of contamination of transgenic plants with the wt virus infections. For this purpose, a silent mutation will be introduced within the 3' noncoding region in the original pB3TP7 plasmid. This plasmid has full-length BMV RNA3 cDNA cloned just downstream to in vitro transcription T7 promoter into the pUC19 bacterial cloning vector.

Control donor RNA construct will be similar to the actual donor RNA but will not have the antisense recombination cassette.

Target RNA will be expressed in transgenic *N. benthamiana* plants as an mRNA molecule. It will contain the entire BMV RNA3 sequence with the exception of the last 200 nucleotides (FIG. 4B). This deletion will remove the initiation site of minus strand synthesis so the RNA construct will not be able to replicate by the use of BMV replicase enzyme. The inability to replicate will then cause that the CP molecule will not be expressed because the latter can be translated only from subgenomic RNA4; subgenomic RNA4 is synthesized during RNA replication process. Consequently, there will be no possibility for complementation of the system with CP molecules expressed in transgenic plants. On the other hand, the upstream 3' noncoding sequences will be retained to assure the formation of local double-stranded region with the inoculated donor RNA.

The above modifications will be done in pB3-34-29 plasmid previously constructed in our laboratory. This plasmid contains full-length BMV cDNA3 sequences cloned in Psi I site of pDH51 vector between CaMV 35S transcription promoter and polyadenylation signals. The last 200 nucleotides will be deleted from cDNA3 fragment by digestion with TthI-SPhI restriction enzymes and religated. The efficient replication of BMV RNAs requires native 5' end sequences. The above constructs contain 20 heterologous (vector) nucleotides between the CaMV 35S promoter transcription initiation site and the first BMV RNA3 nucleotide. These vector sequences will be removed by looping out with PCR and appropriate oligonucleotide primers that amplify a desired 5' BMV cDNA3 fragment. The PCR product will be then religated between engineered restriction sites.

The entire functional unit (CaMV 35S promoter+ truncated BMV cDNA3+polyadenylation signal) will be released from the modified pB3-34-29 plasmid by digestion with EcoRI—KpnI and religated at one of the cloning sites in pGA482 binary vector. Final constructs will be propagated in *E. coli* (DH5α) and used for transformation of Agrobacterium competent cells (see below).

An Agrobacterium-mediated transformation will be used in order to generate *N. benthamiana* plants stably transformed with target BMV RNA sequences. Competent *Agrobacterium tumefaciens* cells (obtained by a $CaCl_2$ treatment similar to that used for preparing *E. coli* competent cells) will be transformed with plasmid DNA (pGA484 derivatives; see above), and the transformed cells will be selected by growing on LB medium with tetracycline. Sterile *N. benthamiana* leaf discs, obtained by punching aseptically, will be first incubated in a swelling medium, then infected with Agrobacterium, the excess of bacterium removed with carbenicillin, and plants regenerated by transferring the discs first to shooting and then to rooting media.

The presence of integrated cDNA sequences will be detected by amplification with PCR using BMV RNA3-specific primers and confirmed by Southern hybridization analysis. Accumulation of corresponding target mRNA molecules will be determined by Northern hybridization.

The recombinational activity of transgenic plants will be tested by mechanical inoculation with a mixture of in vitro transcribed wt BMV RNAs 1 and 2, and donor RNA3. The appearance of viral infection will be first estimated visually by detecting characteristic symptoms on both inoculated and systemic leaves, and the accumulation of viral RNA will be confirmed by dot blot hybridization.

Control inoculations will involve mixtures of transcribed wt BMV RNAs 1 and 2 and control donor RNA3 construct (see above). The lack of systemic infection will further confirm the role of antisense recombination cassettes in targeting efficient recombination events.

The procedure of using in vitro transcripts for induction of viral infection is routinely used for plus-stranded RNA viruses. Specifically, we have tested before the ability of transcribed full-length BMV RNAs to initiate viral infection in *N. benthamiana* plants. 10 μg of each of transcribed RNAs was sufficient to develop BMV infection in seven out of ten inoculated plants.

In view of the above, it will be seen that the several objects of the invention are achieved and other advantageous results attained. As various changes could be made in the above constructs and methods without departing from the scope of the invention, it is intended that all matter contained in the above description or shown in the accompanying drawings shall be interpreted as illustrative and not in a limiting sense.

The following references are incorporated by reference herein:
1. Strauss, J. H. & Strauss, E. G. (1988) *Annu. Rev. Microbiol.* 42, 657–683.
2. King, A. M. Q. (1988) in *RNA Genetics*, eds. Domingo, E., Holland, J. J. & Ahlquist, P. (CRC Press, Boca Raton, Fla.) Vol. 2, pp. 149–165
3. Ahlquist, P., Dasgupta, R. & Kaesberg, P. (1981) *Cell* 23, 183–189.
4. Bujarski, J. J. & Kaesberg, P. (1986) *Nature (London)* 321, 528–531.
5. Bujarski, J. J. & Dzianott, A. M. (1991) *J. Virol.* 65, 4153–4159.
6. Nagy, P. D. & Bujarski, J. J. (1992) *J. Virol.* 66, 6824–6828.
7. Rao, A. L. N., Sullivan, B. P. & Hall, T. C. (1990) *J. Gen. Virol.* 71, 1403–1407.
8. Rao, A. L. N. & Hall, T. C. (1990) *J. Virol.* 64, 2437–2441.
9. Ishikawa, M., Kroner, P., Ahlquist, P. & Meshi, T. (1991) *J. Virol.* 65, 3451–3459.
10. Allison, R., Thompson, C. & Ahlquist, P. (1990) *Proc. Natl. Acad. Sci. USA* 87, 1820–1824.
11. Cascone, P. J., Carpenter, C. D., Li, X. H. & Simon, A. E. (1990) *EMBO J.* 9, 1709–1715.
12. Van der Kuyl, A. C., Neeleman, L. & Bol, J. F. (1991) *Virology* 183, 731–738.
13. Kirkegaard, K. & Baltimore, D. (1986) *Cell* 47, 433–443.
14. Romanova, L. I., Blinov, V. M., Tolskaya, E. A., Victorova, E. G., Kolesnikova, M. S., Guseva, E. A. & Agol, V. I. (1986) *Virology* 155, 202–213.
15. Kuge, S., Saito, I. & Nomoto, A. (1986) *J. Mol. Biol.* 192, 473–487.
16. Makino, S., Keck, J. G., Stohlman, S. A. & Lai, M. M. C. (1986) *J. Virol.* 57, 729–737.
17. Weiss, B. G. & Schlesinger, S. (1991) *J. Virol.* 65, 4017–4025.
18. Munishkin, A. V., Voronin, L. A. & Chetverin, A. B. (1988) *Nature (London)* 333, 473–475.
19. Palasingam, K. & Shaklee, P. N. (1992) *J. Virol.* 66, 2435–2442.
20. Zhang, C., Cascone, P. J. & Simon, A. E. (1991) *Virology* 184, 791–794.
21. Banner, L. R. & Lai, M. M. C. (1991) *Virology* 185, 441–445.
22. Janda, M., French, R. & Ahlquist, P. (1987) *Virology* 158, 259–262.
23. Allison, R. F., Janda, M. & Ahlquist, P. (1988) *J. Virol.* 62, 3581–3588.

24. Sambrook, J., Fritsch, E. F. & Maniatis, T. (1989) *Molecular Cloning: A Laboratory Manual* (Cold Spring Harbor Laboratory Press, Plainview, N.Y.), p. 7.71.
25. Miller, W. A., Bujarski, J. J., Dreher, T. W. & Hall, T. C. (1985) *J. Mol. Biol.* 187, 537–546.
26. Bujarski, J. J., Ahlquist, P., Hall, T. C., Dreher, T. W. & Kaesberg, P. (1986) *EMBO J.* 5, 1769–1774.
27. Lai, M. M. C. (1992) *Microbiol. Rev.* 56, 61–79.
28. Marsh, L. E., Huntley, C. C., Pogue, G. P., Connel, J. P. & Hall, T. C. (1991) *Virology* 182, 76–83.

What is claimed:

1. An RNA-RNA recombination construct comprising a first RNA molecule derived from a single stranded RNA virus, said first RNA molecule having sequences at the 3' end active in forming a complex with RNA polymerase for initiating replication and having a non-naturally occurring sequence at least 25 nucleotides long upstream of the sequences binding the RNA polymerase, said upstream non-naturally occurring sequence being complementary to a sequence in a second target RNA molecule derived from a single stranded RNA virus, said non-naturally occurring sequence in the first RNA being in an antisense orientation to said sequence in the second target RNA, said non-naturally occurring sequence being long enough to hybridize and produce a stable heteroduplex with said target RNA molecule along said said non-naturally occurring sequence whereby recombination efficiency between the first and second RNAs is enhanced when RNA replication is induced.

2. The construct of claim 1 wherein the first RNA molecule is derived from a positive-stranded RNA virus.

3. The construct of claim 2 wherein the first RNA molecule is derived from a positive-stranded RNA virus in the Sindbis superfamily of viruses.

4. The construct of claim 2 wherein the first RNA molecule is derived from a positive-stranded RNA virus in the bromovirus group of viruses.

5. The construct of claim 3 wherein the second RNA molecule is derived from a positive-stranded RNA virus in the Sindbis superfamily of viruses.

6. The construct of claim 4 wherein the second RNA molecule is derived from a positive-stranded RNA in the bromovirus group of viruses.

7. The construct of claim 1 wherein the first RNA molecule is derived from a positive-stranded brome mosaic virus.

8. The construct of claim 7 wherein the second RNA molecule is derived from a positive-stranded brome mosaic virus.

9. A DNA sequence encoding said first RNA molecule of claims 1–8 operably joined to a promoter which controls transcription of said first RNA molecule.

10. A vector with a DNA sequence encoding said first RNA molecule of claims 1–8 operably joined to a promoter which controls transcription of said first RNA molecule.

11. A prokaryotic or eukaryotic host cell transformed or transfected by a vector with a DNA sequence encoding said first RNA molecule of claims 1–8 operably joined to a promoter which controls transcription of said first RNA molecule in at least some of the cells into which the vector is introduced.

12. A transgenic plant transformed or transfected by a vector with a DNA sequence encoding said first RNA molecule of claims 1–8 operably joined to a promoter which controls transcription of said first RNA molecule in at least some of the plants into which the vector is introduced.

13. A method of increasing recombination efficiency comprising:

(a) forming an RNA-RNA recombination construct comprising a first RNA molecule derived from a single stranded RNA virus, said first RNA molecule having sequences at the 3' end active in forming a complex with RNA polymerase for initiating replication and having a non-naturally occurring sequence at least 25 nucleotides long upstream of the sequences capable of binding the RNA polymerase, said upstream non-naturally occurring sequence being complementary to a sequence in a second target RNA molecule derived from a single stranded RNA virus, said non-naturally occurring sequence in the first RNA being in antisense orientation to said sequence in the second target RNA, said non-naturally occurring sequence being long enough to hybridize and produce a stable heteroduplex with said target RNA molecule along said non-naturally occurring sequence;

(b) bringing the construct and said second RNA molecule together whereby the non-naturally occurring sequence and the target sequence form a heteroduplex by base pairing along the non-naturally occurring sequence; and, (c) replicating the construct whereby the heteroduplex enhances recombination efficiency.

14. The method of claim 13 wherein the first RNA molecule is derived from a positive-stranded RNA virus.

15. The method of claim 14 wherein the first RNA molecule is derived from a positive-stranded RNA virus in the Sindbis superfamily of viruses.

16. The method of claim 14 wherein the first RNA molecule is derived from a positive-stranded positive RNA virus in the bromovirus group of viruses.

17. The method of claim 15 wherein the second RNA molecule is derived from a positive-stranded RNA virus in the Sindbis superfamily of viruses.

18. The method of claim 16 wherein the second RNA molecule is derived from a positive-stranded RNA in the bromovirus group of viruses.

19. The method of claim 13 wherein the first RNA molecule is derived from a positive-stranded brome mosaic virus.

20. The method of claim 19 wherein the second RNA molecule is derived from a positive-stranded brome mosaic virus.

21. A method of increasing recombination efficiency comprising:

(a) transcribing a purified and isolated cDNA sequence which encodes a first RNA molecule derived from a single stranded RNA virus that is active in initiating replication and having a non-naturally occurring sequence at least 25 nucleotides long complementary to a sequence in a second target RNA molecule derived from a single stranded RNA virus, said non-naturally occurring sequence being in an antisense orientation to the sequence in said target RNA molecule;

(b) bringing the RNA transcript and said second RNA molecule together whereby the non-naturally occurring sequence and the target sequence form a heteroduplex; and, (c) replicating the transcript whereby the heteroduplex enhances recombination efficiency.

22. The method of claim 21 wherein the first RNA molecule is derived from a positive-stranded RNA virus.

23. The method of claim 22 wherein the first RNA molecule is derived from a positive-stranded RNA virus in the Sindbis superfamily of viruses.

24. The method of claim 22 wherein the first RNA molecule is derived from a positive-stranded RNA virus in the bromovirus group of viruses.

25. The method of claim 23 wherein the second RNA molecule is derived from a positive-stranded RNA virus in the Sindbis superfamily of viruses.

26. The method of claim 24 wherein the second RNA molecule is derived from a positive-stranded RNA in the bromovirus group of viruses.

27. The method of claim 21 wherein the first RNA molecule is derived from a positive-stranded brome mosaic virus.

28. The method of claim 27 wherein the second RNA molecule is derived from a positive-stranded brome mosaic virus.

* * * * *

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
        ( A ) LENGTH: 161 bases
        ( B ) TYPE: nucleic
        ( C ) STRANDEDNESS: single
        ( D ) TOPOLOGY: linear ( i i ) MOLECULE TYPE: viral RNA
        ( A ) DESCRIPTION: recombinant BMV RNA3

( i i i ) HYPOTHETICAL: yes ( i v ) ANTI-SENSE: yes ( v ) FRAGMENT TYPE:

( v i ) ORIGINAL SOURCE:
        ( A ) ORGANISM: brome mosaic virus
        ( B ) STRAIN: Madison
        ( C ) INDIVIDUAL ISOLATE: M1
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY: no
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY: upper strand capable of forming a heteroduplex
            with SEQ ID 2 (het in Fig. 3)
        ( B ) LOCATION:
        ( C ) IDENTIFICATION METHOD: cDNA sequencing
        ( D ) OTHER INFORMATION:

( x ) PUBLICATION INFORMATION:
        ( A ) AUTHORS: Nagy, P.D.
            Bujarski, J.J.
        ( B ) TITLE:Targeting the site of RNA- RNA recombination in virus
            with antisense sequences
        ( C ) JOURNAL: Proc. Natl. Acad. Sci. USA
        ( D ) VOLUME: 90
        ( E ) ISSUE:
        ( F ) PAGES: 6390-6394
        ( G ) DATE: July 1993
        ( H ) DOCUMENT NUMBER:
        ( I ) FILING DATE:
        ( J ) PUBLICATION DATE: July 1993
        ( K ) RELEVANT RESIDUES IN SEQ ID NO: 140

( x i ) SEQUENCE DESCRIPTION: SEQ ID NO:1:

```
CCCUGCUCGG  AGGACUAGUC  GAGCAGAGGU  CUCACACAGA  GACAAGCGCA  UCACUUAACA      60

CAAUUAAAGA  UCAAAUCACC  AGCGAGCUCG  CCGUUAAAGC  AAUACUCAAA  GGACUUCUUG     120
```

UGUCGUGUUA AGGCAACCAA ACAGUACUCC UCAUGUUUCU A       161

( 2 ) INFORMATION FOR SEQ ID NO:2:

( i ) SEQUENCE CHARACTERISTICS:
        ( A ) LENGTH: 152 bases
        ( B ) TYPE: nucleic
        ( C ) STRANDEDNESS: single
        ( D ) TOPOLOGY: linear ( i i ) MOLECULE TYPE: viral RNA
        ( A ) DESCRIPTION: BMV RNA1 (wt)

( i i i ) HYPOTHETICAL: no ( i v ) ANTI-SENSE:

( v ) FRAGMENT TYPE:

( v i ) ORIGINAL SOURCE:
        ( A ) ORGANISM: brome mosaic virus
        ( B ) STRAIN: Madison
        ( C ) INDIVIDUAL ISOLATE: M1
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY: no
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY: lower strand capable of forming a heteroduplex
            with SEQ ID 1 (het in Fig. 3)
        ( B ) LOCATION:
        ( C ) IDENTIFICATION METHOD: cDNA sequencing
        ( D ) OTHER INFORMATION:

( x ) PUBLICATION INFORMATION:
        ( A ) AUTHORS: Nagy, P.D.
            Bujarski, J.J.
        ( B ) TITLE:Targeting the site of RNA- RNA recombination in virus
            with antisense sequences
        ( C ) JOURNAL: Proc. Natl. Acad. Sci. USA
        ( D ) VOLUME: 90
        ( E ) ISSUE:
        ( F ) PAGES: 6390-6394
        ( G ) DATE: July 1993
        ( H ) DOCUMENT NUMBER:
        ( I ) FILING DATE:
        ( J ) PUBLICATION DATE: July 1993
        ( K ) RELEVANT RESIDUES IN SEQ ID NO: 140

( x i ) SEQUENCE DESCRIPTION: SEQ ID NO:2:

UUUAAACAUG AGGAGUACUG UUUGGUUGCC UUAACACGAC ACAAGAAGUC CUUUGAGUAU       60

UGCUUUAACG GCGAGCUCGC UGGUGAUUUG AUCUUUAAUU GUGUUAAGUG AUGCGCUUGU       120

CUCUGUGUGA GACCUCUGCU CGAGGAGAGC CC       152

( 2 ) INFORMATION FOR SEQ ID NO:3:

( i ) SEQUENCE CHARACTERISTICS:
        ( A ) LENGTH: 89 bases
        ( B ) TYPE: nucleic
        ( C ) STRANDEDNESS: single
        ( D ) TOPOLOGY: linear ( i i ) MOLECULE TYPE: viral RNA (A) DESCRIPTION: recombinant BMV RNA3

(iii) HYPOTHETICAL: yes (iv) ANTI-SENSE: yes (v) FRAGMENT TYPE:

(vi) ORIGINAL SOURCE:
                (A) ORGANISM: brome mosaic virus
                (B) STRAIN: Madison
                (C) INDIVIDUAL ISOLATE: M1
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY: no
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY: upper strand capable of forming a heteroduplex
                    with SEQ ID 4 (het in Fig. 3)
                (B) LOCATION:
                (C) IDENTIFICATION METHOD: cDNA sequencing
                (D) OTHER INFORMATION:

(x) PUBLICATION INFORMATION:
                (A) AUTHORS: Nagy, P.D.
                    Bujarski, J.J.
                (B) TITLE: Targeting the site of RNA-RNA recombination in virus
                    with antisense sequences
                (C) JOURNAL: Proc. Natl. Acad. Sci. USA
                (D) VOLUME: 90
                (E) ISSUE:
                (F) PAGES: 6390-6394
                (G) DATE: July 1993
                (H) DOCUMENT NUMBER:
                (I) FILING DATE:
                (J) PUBLICATION DATE: July 1993
                (K) RELEVANT RESIDUES IN SEQ ID NO: 66

(xi) SEQUENCE DESCRIPTION: SEQ ID NO:3:

CCCUGCUCGG AGGACUAGUC UCGAGCAGAG GUCUCACACA GAGACAAGCG CAUCACUUAA         60

CACAAUUAAA GAUCAAAUCA CCAGCGACU                                          89

(2) INFORMATION FOR SEQ ID NO:4:

(i) SEQUENCE CHARACTERISTICS:
                (A) LENGTH: 78 bases
                (B) TYPE: nucleic
                (C) STRANDEDNESS: single
                (D) TOPOLOGY: linear (ii) MOLECULE TYPE: viral RNA
                (A) DESCRIPTION: BMV RNA1 (wt)

(iii) HYPOTHETICAL: no (iv) ANTI-SENSE:

(v) FRAGMENT TYPE:

(vi) ORIGINAL SOURCE:
                (A) ORGANISM: brome mosaic virus
                (B) STRAIN: Madison
                (C) INDIVIDUAL ISOLATE: M1
                (D) DEVELOPMENTAL STAGE:
                (E) HAPLOTYPE:

( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY: no
                    ( B ) CLONE:

( v i i i ) POSITION IN GENOME:
                    ( A ) CHROMOSOME/SEGMENT:
                    ( B ) MAP POSITION: BMV RNA1
                    ( C ) UNITS:

( i x ) FEATURE:
                    ( A ) NAME/KEY: lower strand capable of forming a heteroduplex
                            with SEQ ID 3 (het in Fig. 3)
                    ( B ) LOCATION:
                    ( C ) IDENTIFICATION METHOD: cDNA sequencing
                    ( D ) OTHER INFORMATION:

( x ) PUBLICATION INFORMATION:
                    ( A ) AUTHORS: Nagy, P.D.
                            Bujarski, J.J.
                    ( B ) TITLE:Targeting the site of RNA- RNA recombination in virus
                            with antisense sequences
                    ( C ) JOURNAL: Proc. Natl. Acad. Sci. USA
                    ( D ) VOLUME: 90
                    ( E ) ISSUE:
                    ( F ) PAGES: 6390-6394
                    ( G ) DATE: July 1993
                    ( H ) DOCUMENT NUMBER:
                    ( I ) FILING DATE:
                    ( J ) PUBLICATION DATE: July 1993
                    ( K ) RELEVANT RESIDUES IN SEQ ID NO: 66

( x i ) SEQUENCE DESCRIPTION: SEQ ID NO:4:

GCUCGCUGGU    GAUUUGAUCU    UUAAUUGUGU    UAAGUGAUGC    GCUUGUCUCU    GUGUGAGACC        6 0

UCUGCUCGAG    GAGAGCCC        7 8

( 2 ) INFORMATION FOR SEQ ID NO:5:

( i ) SEQUENCE CHARACTERISTICS:
                    ( A ) LENGTH: 60 bases
                    ( B ) TYPE: nucleic
                    ( C ) STRANDEDNESS: single
                    ( D ) TOPOLOGY: linear ( i i ) MOLECULE TYPE: viral RNA
                    ( A ) DESCRIPTION: recombinant BMV RNA3

( i i i ) HYPOTHETICAL: yes ( i v ) ANTI-SENSE: yes ( v ) FRAGMENT TYPE:

( v i ) ORIGINAL SOURCE:
                    ( A ) ORGANISM: brome mosaic virus
                    ( B ) STRAIN: Madison
                    ( C ) INDIVIDUAL ISOLATE: M1
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY: no
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                ( A ) NAME/KEY: upper strand capable of forming a heteroduplex
                      with SEQ ID 6 (het in Fig. 3)
                ( B ) LOCATION:
                ( C ) IDENTIFICATION METHOD: cDNA sequencing
                ( D ) OTHER INFORMATION:

( x ) PUBLICATION INFORMATION:
                ( A ) AUTHORS: Nagy, P.D.
                      Bujarski, J.J.
                ( B ) TITLE:Targeting the site of RNA- RNA recombination in virus
                      with antisense sequences
                ( C ) JOURNAL: Proc. Natl. Acad. Sci. USA
                ( D ) VOLUME: 90
                ( E ) ISSUE:
                ( F ) PAGES: 6390-6394
                ( G ) DATE: July 1993
                ( H ) DOCUMENT NUMBER:
                ( I ) FILING DATE:
                ( J ) PUBLICATION DATE: July 1993
                ( K ) RELEVANT RESIDUES IN SEQ ID NO: 40

( x i ) SEQUENCE DESCRIPTION: SEQ ID NO:5:

CCCUGCUCGG  AGGACUAGUC  UCGAGCAGAG  GUCUCACACA  GAGACAAGCG  CAUCACUUAA        60

( 2 ) INFORMATION FOR SEQ ID NO:6:

( i ) SEQUENCE CHARACTERISTICS:
                ( A ) LENGTH: 52 bases
                ( B ) TYPE: nucleic
                ( C ) STRANDEDNESS: single
                ( D ) TOPOLOGY: linear ( i i ) MOLECULE TYPE: viral RNA
                ( A ) DESCRIPTION: BMV RNA1 (wt)

( i i i ) HYPOTHETICAL: no ( i v ) ANTI-SENSE:

( v ) FRAGMENT TYPE:

( v i ) ORIGINAL SOURCE:
                ( A ) ORGANISM: brome mosaic virus
                ( B ) STRAIN: Madison
                ( C ) INDIVIDUAL ISOLATE: M1
                ( D ) DEVELOPMENTAL STAGE:
                ( E ) HAPLOTYPE:
                ( F ) TISSUE TYPE:
                ( G ) CELL TYPE:
                ( H ) CELL LINE:
                ( I ) ORGANELLE:

( v i i ) IMMEDIATE SOURCE:
                ( A ) LIBRARY: no
                ( B ) CLONE:

( v i i i ) POSITION IN GENOME:
                ( A ) CHROMOSOME/SEGMENT:
                ( B ) MAP POSITION: BMV RNA1
                ( C ) UNITS:

( i x ) FEATURE:
                ( A ) NAME/KEY: lower strand capable of forming a heteroduplex
                      with SEQ ID 5 (het in Fig. 3)
                ( B ) LOCATION:
                ( C ) IDENTIFICATION METHOD: cDNA sequencing
                ( D ) OTHER INFORMATION:

( x ) PUBLICATION INFORMATION:
                ( A ) AUTHORS: Nagy, P.D.
                      Bujarski, J.J.
                ( B ) TITLE:Targeting the site of RNA- RNA recombination in virus
                      with antisense sequences
                ( C ) JOURNAL: Proc. Natl. Acad. Sci. USA
                ( D ) VOLUME: 90
                ( E ) ISSUE:
                ( F ) PAGES: 6390-6394

(G) DATE: July 1993
                    (H) DOCUMENT NUMBER:
                    (I) FILING DATE:
                    (J) PUBLICATION DATE: July 1993
                    (K) RELEVANT RESIDUES IN SEQ ID NO: 40

(x i) SEQUENCE DESCRIPTION: SEQ ID NO:6:

GUGUUAAGUG AUGCGCUUGU CUCUGUGUGA GACCUCUGCU CGAGGAGAGC CC            52

(2) INFORMATION FOR SEQ ID NO:7:

(i) SEQUENCE CHARACTERISTICS:
                    (A) LENGTH: 53 bases
                    (B) TYPE: nucleic
                    (C) STRANDEDNESS: single
                    (D) TOPOLOGY: linear (ii) MOLECULE TYPE: viral RNA
                    (A) DESCRIPTION: recombinant BMV RNA3

(iii) HYPOTHETICAL: yes (iv) ANTI-SENSE: yes (v) FRAGMENT TYPE:

(vi) ORIGINAL SOURCE:
                    (A) ORGANISM: brome mosaic virus
                    (B) STRAIN: Madison
                    (C) INDIVIDUAL ISOLATE: M1
                    (D) DEVELOPMENTAL STAGE:
                    (E) HAPLOTYPE:
                    (F) TISSUE TYPE:
                    (G) CELL TYPE:
                    (H) CELL LINE:
                    (I) ORGANELLE:

(vii) IMMEDIATE SOURCE:
                    (A) LIBRARY: no
                    (B) CLONE:

(viii) POSITION IN GENOME:
                    (A) CHROMOSOME/SEGMENT:
                    (B) MAP POSITION:
                    (C) UNITS:

(ix) FEATURE:
                    (A) NAME/KEY: upper strand capable of forming a heteroduplex
                        with SEQ ID 8 (het in Fig. 3).
                    (B) LOCATION:
                    (C) IDENTIFICATION METHOD: cDNA sequencing
                    (D) OTHER INFORMATION:

(x) PUBLICATION INFORMATION:
                    (A) AUTHORS: Nagy, P.D.
                                 Bujarski, J.J.
                    (B) TITLE:Targeting the site of RNA- RNA recombination in virus
                        with antisense sequences
                    (C) JOURNAL: Proc. Natl. Acad. Sci. USA
                    (D) VOLUME: 90
                    (E) ISSUE:
                    (F) PAGES: 6390-6394
                    (G) DATE: July 1993
                    (H) DOCUMENT NUMBER:
                    (I) FILING DATE:
                    (J) PUBLICATION DATE: July 1993
                    (K) RELEVANT RESIDUES IN SEQ ID NO: 30

(x i) SEQUENCE DESCRIPTION: SEQ ID NO:7:

CCCUGCUCGG AGGACUAGUC UCGAGCAGAG GUCUCACACA GAGACAAGCG ACU           53

(2) INFORMATION FOR SEQ ID NO:8:

(i) SEQUENCE CHARACTERISTICS:
                    (A) LENGTH: 42 bases
                    (B) TYPE: nucleic ( C ) STRANDEDNESS: single
                    ( D ) TOPOLOGY: linear ( i i ) MOLECULE TYPE: viral RNA
                    ( A ) DESCRIPTION: BMV RNA1 (wt)

( i i i ) HYPOTHETICAL: no ( i v ) ANTI-SENSE:

( v ) FRAGMENT TYPE:

( v i ) ORIGINAL SOURCE:
                    ( A ) ORGANISM: brome mosaic virus
                    ( B ) STRAIN: Madison
                    ( C ) INDIVIDUAL ISOLATE: M1
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY: no
                    ( B ) CLONE:

( v i i i ) POSITION IN GENOME:
                    ( A ) CHROMOSOME/SEGMENT:
                    ( B ) MAP POSITION: BMV RNA1
                    ( C ) UNITS:

( i x ) FEATURE:
                    ( A ) NAME/KEY: lower strand capable of forming a heteroduplex
                            with SEQ ID 7 (het in Fig. 3)
                    ( B ) LOCATION:
                    ( C ) IDENTIFICATION METHOD: cDNA sequencing
                    ( D ) OTHER INFORMATION:

( x ) PUBLICATION INFORMATION:
                    ( A ) AUTHORS: Nagy, P.D.
                                Bujarski, J.J.
                    ( B ) TITLE:Targeting the site of RNA- RNA recombination in virus
                            with antisense sequences
                    ( C ) JOURNAL: Proc. Natl. Acad. Sci. USA
                    ( D ) VOLUME: 90
                    ( E ) ISSUE:
                    ( F ) PAGES: 6390-6394
                    ( G ) DATE: July 1993
                    ( H ) DOCUMENT NUMBER:
                    ( I ) FILING DATE:
                    ( J ) PUBLICATION DATE: July 1993
                    ( K ) RELEVANT RESIDUES IN SEQ ID NO: 30

( x i ) SEQUENCE DESCRIPTION: SEQ ID NO:8:

AUGCGCUUGU CUGUGUGUGA GACCUCUGCU CGAGGAGAGC CC                                                      4 2

( 2 ) INFORMATION FOR SEQ ID NO:9:

( i ) SEQUENCE CHARACTERISTICS:
                    ( A ) LENGTH: 43 bases
                    ( B ) TYPE: nucleic
                    ( C ) STRANDEDNESS: single
                    ( D ) TOPOLOGY: linear ( i i ) MOLECULE TYPE: viral RNA
                    ( A ) DESCRIPTION: recombinant BMV RNA3

( i i i ) HYPOTHETICAL: yes ( i v ) ANTI-SENSE: yes ( v ) FRAGMENT TYPE:

( v i ) ORIGINAL SOURCE:
                    ( A ) ORGANISM: brome mosaic virus
                    ( B ) STRAIN: Madison
                    ( C ) INDIVIDUAL ISOLATE: M1

(D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY: no
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY: upper strand capable of forming a heteroduplex
                    with SEQ ID 10 (he in Fig. 3)
                (B) LOCATION:
                (C) IDENTIFICATION METHOD: cDNA sequencing
                (D) OTHER INFORMATION:

(x) PUBLICATION INFORMATION:
                (A) AUTHORS: Nagy, P.D.
                             Bujarski, J.J.
                (B) TITLE: Targeting the site of RNA- RNA recombination in virus
                    with antisense sequences
                (C) JOURNAL: Proc. Natl. Acad. Sci. USA
                (D) VOLUME: 90
                (E) ISSUE:
                (F) PAGES: 6390-6394
                (G) DATE: July 1993
                (H) DOCUMENT NUMBER:
                (I) FILING DATE:
                (J) PUBLICATION DATE: July 1993
                (K) RELEVANT RESIDUES IN SEQ ID NO: 20

(xi) SEQUENCE DESCRIPTION: SEQ ID NO:9:

CCCUGCUCGG AGGACUAGUC UCGAGCAGAG GUCUCACACA ACU                                    43

(2) INFORMATION FOR SEQ ID NO:10:

(i) SEQUENCE CHARACTERISTICS:
                (A) LENGTH: 32 bases
                (B) TYPE: nucleic
                (C) STRANDEDNESS: single
                (D) TOPOLOGY: linear (ii) MOLECULE TYPE: viral RNA
                (A) DESCRIPTION: BMV RNA1 (wt)

(iii) HYPOTHETICAL: no (iv) ANTI-SENSE:

(v) FRAGMENT TYPE:

(vi) ORIGINAL SOURCE:
                (A) ORGANISM: brome mosaic virus
                (B) STRAIN: Madison
                (C) INDIVIDUAL ISOLATE: M1
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY: no
                (B) CLONE:

(viii) POSITION IN GENOME:
                (A) CHROMOSOME/SEGMENT:
                (B) MAP POSITION: BMV RNA1
                (C) UNITS:

( i x ) FEATURE:
    ( A ) NAME/KEY: lower strand capable of forming a heteroduplex with SEQ ID 9 (het in Fig. 3)
    ( B ) LOCATION:
    ( C ) IDENTIFICATION METHOD: cDNA sequencing
    ( D ) OTHER INFORMATION:

( x ) PUBLICATION INFORMATION:
    ( A ) AUTHORS: Nagy, P.D.
            Bujarski, J.J.
    ( B ) TITLE:Targeting the site of RNA- RNA recombination in virus with antisense sequences
    ( C ) JOURNAL: Proc. Natl. Acad. Sci. USA
    ( D ) VOLUME: 90
    ( E ) ISSUE:
    ( F ) PAGES: 6390-6394
    ( G ) DATE: July 1993
    ( H ) DOCUMENT NUMBER:
    ( I ) FILING DATE:
    ( J ) PUBLICATION DATE: July 1993
    ( K ) RELEVANT RESIDUES IN SEQ ID NO: 20

( x i ) SEQUENCE DESCRIPTION: SEQ ID NO:10:

```
CUCUGUGUGA  GACCUCUGCU  CGAGGAGAGC  CC                                  32
```

( 2 ) INFORMATION FOR SEQ ID NO:11:

( i ) SEQUENCE CHARACTERISTICS:
        ( A ) LENGTH: 163 bases
        ( B ) TYPE: nucleic
        ( C ) STRANDEDNESS: single
        ( D ) TOPOLOGY: linear ( i i ) MOLECULE TYPE: viral RNA
        ( A ) DESCRIPTION: recombinant BMV RNA3

( i i i ) HYPOTHETICAL: yes ( i v ) ANTI-SENSE: yes ( v ) FRAGMENT TYPE:

( v i ) ORIGINAL SOURCE:
        ( A ) ORGANISM: brome mosaic virus
        ( B ) STRAIN: Madison
        ( C ) INDIVIDUAL ISOLATE: M1
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY: no
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY: upper strand capable of forming a heteroduplex with SEQ ID 12 (het in Fig. 3)
        ( B ) LOCATION:
        ( C ) IDENTIFICATION METHOD: cDNA sequencing
        ( D ) OTHER INFORMATION:

( x ) PUBLICATION INFORMATION:
        ( A ) AUTHORS: Nagy, P.D.
                Bujarski, J.J.
        ( B ) TITLE:Targeting the site of RNA- RNA recombination in virus with antisense sequences
        ( C ) JOURNAL: Proc. Natl. Acad. Sci. USA
        ( D ) VOLUME: 90
        ( E ) ISSUE:
        ( F ) PAGES: 6390-6394

(G) DATE: July 1993
(H) DOCUMENT NUMBER:
(I) FILING DATE:
(J) PUBLICATION DATE: July 1993
(K) RELEVANT RESIDUES IN SEQ ID NO: 140

(x i) SEQUENCE DESCRIPTION: SEQ ID NO:11:

| | | | | | | |
|---|---|---|---|---|---|---|
| CCCUGCUCGG | AGGACUAGUC | UCGAGCAGAG | GUUUUAUAUA | GAGACAAGCG | CAUCACUUAA | 60 |
| CACAAUUAAA | GAUCAAAUCA | CCAGCGAGCU | CGCCGUUAAA | GCAAUACUCA | AAGGACUUCU | 120 |
| UGUGUCGUGU | UAAGGCAACC | AAACAGUACU | CCUCAUGUUU | CUA | | 163 |

(2) INFORMATION FOR SEQ ID NO:12:

(i) SEQUENCE CHARACTERISTICS:
        (A) LENGTH: 152 bases
        (B) TYPE: nucleic
        (C) STRANDEDNESS: single
        (D) TOPOLOGY: linear (i i) MOLECULE TYPE: viral RNA
        (A) DESCRIPTION: BMV RNA1(wt)

(i i i) HYPOTHETICAL: no (i v) ANTI-SENSE:

(v) FRAGMENT TYPE:

(v i) ORIGINAL SOURCE:
        (A) ORGANISM: brome mosaic virus
        (B) STRAIN: Madison
        (C) INDIVIDUAL ISOLATE: M1
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(v i i) IMMEDIATE SOURCE:
        (A) LIBRARY: no
        (B) CLONE:

(v i i i) POSITION IN GENOME:
        (A) CHROMOSOME/SEGMENT:
        (B) MAP POSITION: BMV RNA1
        (C) UNITS:

(i x) FEATURE:
        (A) NAME/KEY: lower strand capable of forming a heteroduplex
            with SEQ ID 11 (het in Fig. 3)
        (B) LOCATION:
        (C) IDENTIFICATION METHOD: cDNA sequencing
        (D) OTHER INFORMATION:

(x) PUBLICATION INFORMATION:
        (A) AUTHORS: Nagy, P.D.
                      Bujarski, J.J.
        (B) TITLE:Targeting the site of RNA- RNA recombination in virus
            with antisense sequences
        (C) JOURNAL: Proc. Natl. Acad. Sci. USA
        (D) VOLUME: 90
        (E) ISSUE:
        (F) PAGES: 6390-6394
        (G) DATE: July 1993
        (H) DOCUMENT NUMBER:
        (I) FILING DATE:
        (J) PUBLICATION DATE: July 1993
        (K) RELEVANT RESIDUES IN SEQ ID NO: 140

(x i) SEQUENCE DESCRIPTION: SEQ ID NO:12:

| | | | | | | |
|---|---|---|---|---|---|---|
| UUUAAACAUG | AGGAGUACUG | UUUGGUUGCC | UUAACACGAC | ACAAGAAGUC | CUUUGAGUAU | 60 |
| UGCUUUAACG | GCGAGCUCGC | UGGUGAUUUG | AUCUUUAAUU | GUGUUAAGUG | AUGCGCUUGU | 120 |

CUCUGUGUGA GACCUCUGCU CGAGGAGAGC CC                                                                    152

(2) INFORMATION FOR SEQ ID NO:13:

(i) SEQUENCE CHARACTERISTICS:
        (A) LENGTH: 161 bases
        (B) TYPE: nucleic
        (C) STRANDEDNESS: single
        (D) TOPOLOGY: linear (ii) MOLECULE TYPE: viral RNA
        (A) DESCRIPTION: recombinant BMV RNA3

(iii) HYPOTHETICAL: yes (iv) ANTI-SENSE: yes (v) FRAGMENT TYPE:

(vi) ORIGINAL SOURCE:
        (A) ORGANISM: brome mosaic virus
        (B) STRAIN: Madison
        (C) INDIVIDUAL ISOLATE: M1
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY: no
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY: upper strand capable of forming a heteroduplex
            with SEQ ID 14 (het in Fig. 3)
        (B) LOCATION:
        (C) IDENTIFICATION METHOD: cDNA sequencing
        (D) OTHER INFORMATION:

(x) PUBLICATION INFORMATION:
        (A) AUTHORS: Nagy, P.D.
            Bujarski, J.J.
        (B) TITLE:Targeting the site of RNA- RNA recombination in virus
            with antisense sequences
        (C) JOURNAL: Proc. Natl. Acad. Sci. USA
        (D) VOLUME: 90
        (E) ISSUE:
        (F) PAGES: 6390-6394
        (G) DATE: July 1993
        (H) DOCUMENT NUMBER:
        (I) FILING DATE:
        (J) PUBLICATION DATE: July 1993
        (K) RELEVANT RESIDUES IN SEQ ID NO: 136

(xi) SEQUENCE DESCRIPTION: SEQ ID NO:13:

CCCUGCUCGG AGGACUAGUC UCGAGGUCUC ACAGGAUCCA GACAAGCGCA UCACUUAACA     60

CAAUUAAAGA UCAAAUCACC AGCGAGCUCG CCGUUAAAGC AAUACUCAAA GGACUUCUUG    120

UGUCGUGUUA AGGCAACCAA ACAGUACUCC UCAUGUUUCU A                       161

(2) INFORMATION FOR SEQ ID NO:14:

(i) SEQUENCE CHARACTERISTICS:
        (A) LENGTH: 152 bases
        (B) TYPE: nucleic
        (C) STRANDEDNESS: single
        (D) TOPOLOGY: linear (ii) MOLECULE TYPE: viral RNA (A) DESCRIPTION: BMV RNA1 (wt)

(iii) HYPOTHETICAL: no (iv) ANTI-SENSE:

(v) FRAGMENT TYPE:

(vi) ORIGINAL SOURCE:
  (A) ORGANISM: brome mosaic virus
  (B) STRAIN: Madison
  (C) INDIVIDUAL ISOLATE: M1
  (D) DEVELOPMENTAL STAGE:
  (E) HAPLOTYPE:
  (F) TISSUE TYPE:
  (G) CELL TYPE:
  (H) CELL LINE:
  (I) ORGANELLE:

(vii) IMMEDIATE SOURCE:
  (A) LIBRARY: no
  (B) CLONE:

(viii) POSITION IN GENOME:
  (A) CHROMOSOME/SEGMENT:
  (B) MAP POSITION: BMV RNA1
  (C) UNITS:

(ix) FEATURE:
  (A) NAME/KEY: lower strand capable of formed a heteroduplex
      with SEQ ID 13 (het in Fig. 3)
  (B) LOCATION:
  (C) IDENTIFICATION METHOD: cDNA sequencing
  (D) OTHER INFORMATION:

(x) PUBLICATION INFORMATION:
  (A) AUTHORS: Nagy, P.D.
              Bujarski, J.J.
  (B) TITLE: Targeting the site of RNA- RNA recombination in virus
             with antisense sequences
  (C) JOURNAL: Proc. Natl. Acad. Sci. USA
  (D) VOLUME: 90
  (E) ISSUE:
  (F) PAGES: 6390-6394
  (G) DATE: July 1993
  (H) DOCUMENT NUMBER:
  (I) FILING DATE:
  (J) PUBLICATION DATE: July 1993
  (K) RELEVANT RESIDUES IN SEQ ID NO: 136

(xi) SEQUENCE DESCRIPTION: SEQ ID NO:14:

| | | | | | | |
|---|---|---|---|---|---|---|
| UUUAAACAUG | AGGAGUACUG | UUUGGUUGCC | UUAACACGAC | ACAAGAAGUC | CUUUGAGUAU | 60 |
| UGCUUUAACG | GCGAGCUCGC | UGGUGAUUUG | AUCUUUAAUU | GUGUUAAGUG | AUGCGCUUGU | 120 |
| CUCUGUGUGA | GACCUCUGCU | CGAGGAGAGC | CC | | | 152 |

(2) INFORMATION FOR SEQ ID NO:15:

(i) SEQUENCE CHARACTERISTICS:
  (A) LENGTH: 166 bases
  (B) TYPE: nucleic
  (C) STRANDEDNESS: single
  (D) TOPOLOGY: linear (ii) MOLECULE TYPE: viral RNA
  (A) DESCRIPTION: recombinant BMV RNA3

(iii) HYPOTHETICAL: yes (iv) ANTI-SENSE: yes (v) FRAGMENT TYPE:

(vi) ORIGINAL SOURCE:
  (A) ORGANISM: brome mosaic virus
  (B) STRAIN: Madison
  (C) INDIVIDUAL ISOLATE: M1

( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY: no
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY: upper strand capable of forming a heteroduplex
                            with SEQ ID 16 (het in Fig. 3)
                    ( B ) LOCATION:
                    ( C ) IDENTIFICATION METHOD: cDNA sequencing
                    ( D ) OTHER INFORMATION:

( x ) PUBLICATION INFORMATION:
                    ( A ) AUTHORS: Nagy, P.D.
                            Bujarski, J.J.
                    ( B ) TITLE:Targeting the site of RNA- RNA recombination in virus
                            with antisense sequences
                    ( C ) JOURNAL: Proc. Natl. Acad. Sci. USA
                    ( D ) VOLUME: 90
                    ( E ) ISSUE:
                    ( F ) PAGES: 6390-6394
                    ( G ) DATE: July 1993
                    ( H ) DOCUMENT NUMBER:
                    ( I ) FILING DATE:
                    ( J ) PUBLICATION DATE: July 1993
                    ( K ) RELEVANT RESIDUES IN SEQ ID NO: 141

( x i ) SEQUENCE DESCRIPTION: SEQ ID NO:15:

CCCUGCUCGG    AGGACUAGUC    UCGAGGUCUC    ACAGGAUCCA    GACAAGCGAC    GCGUACUUAA         60

CACGCUAGCU    AAAGAUCAAA    UCACCAGCGA    GCUCGCCGUU    AAAGCAAUAC    UCAAAGGACU        120

UCUUGUGUCG    UGUUAAGGCA    ACCAAACAGU    ACUCCUCAUG    UUUCUA                          166

( 2 ) INFORMATION FOR SEQ ID NO:16:

( i ) SEQUENCE CHARACTERISTICS:
                    ( A ) LENGTH: 152 bases
                    ( B ) TYPE: nucleic
                    ( C ) STRANDEDNESS: single
                    ( D ) TOPOLOGY: linear ( i i ) MOLECULE TYPE: viral RNA
                    ( A ) DESCRIPTION: BMV RNA1 (wt)

( i i i ) HYPOTHETICAL: no ( i v ) ANTI-SENSE:

( v ) FRAGMENT TYPE:

( v i ) ORIGINAL SOURCE:
                    ( A ) ORGANISM: brome mosaic virus
                    ( B ) STRAIN: Madison
                    ( C ) INDIVIDUAL ISOLATE: M1
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY: no
                    ( B ) CLONE:

( v i i i ) POSITION IN GENOME:

( A ) CHROMOSOME/SEGMENT:
                ( B ) MAP POSITION: BMV RNA1
                ( C ) UNITS:

( i x ) FEATURE:
                ( A ) NAME/KEY: lower strand capable of forming a heteroduplex
                        with SEQ ID 15 (het in Fig. 3)
                ( B ) LOCATION:
                ( C ) IDENTIFICATION METHOD: cDNA sequencing
                ( D ) OTHER INFORMATION:

( x ) PUBLICATION INFORMATION:
                ( A ) AUTHORS: Nagy, P.D.
                        Bujarski, J.J.
                ( B ) TITLE:Targeting the site of RNA- RNA recombination in virus
                        with antisense sequences
                ( C ) JOURNAL: Proc. Natl. Acad. Sci. USA
                ( D ) VOLUME: 90
                ( E ) ISSUE:
                ( F ) PAGES: 6390-6394
                ( G ) DATE: July 1993
                ( H ) DOCUMENT NUMBER:
                ( I ) FILING DATE:
                ( J ) PUBLICATION DATE: July 1993
                ( K ) RELEVANT RESIDUES IN SEQ ID NO: 141

( x i ) SEQUENCE DESCRIPTION: SEQ ID NO:16:

UUUAAACAUG   AGGAGUACUG   UUUGGUUGCC   UUAACACGAC   ACAAGAAGUC   CUUUGAGUAU        6 0

UGCUUUAACG   GCGAGCUCGC   UGGUGAUUUG   AUCUUUAAUU   GUGUUAAGUG   AUGCGCUUGU        1 2 0

CUCUGUGUGA   GACCUCUGCU   CGAGGAGAGC   CC                                         1 5 2

( 2 ) INFORMATION FOR SEQ ID NO:17:

( i ) SEQUENCE CHARACTERISTICS:
                ( A ) LENGTH: 87 bases
                ( B ) TYPE: nucleic
                ( C ) STRANDEDNESS: single
                ( D ) TOPOLOGY: linear ( i i ) MOLECULE TYPE: viral RNA
                ( A ) DESCRIPTION: recombinant BMV RNA3

( i i i ) HYPOTHETICAL: yes ( i v ) ANTI-SENSE: yes ( v ) FRAGMENT TYPE:

( v i ) ORIGINAL SOURCE:
                ( A ) ORGANISM: brome mosaic virus
                ( B ) STRAIN: Madison
                ( C ) INDIVIDUAL ISOLATE: M1
                ( D ) DEVELOPMENTAL STAGE:
                ( E ) HAPLOTYPE:
                ( F ) TISSUE TYPE:
                ( G ) CELL TYPE:
                ( H ) CELL LINE:
                ( I ) ORGANELLE:

( v i i ) IMMEDIATE SOURCE:
                ( A ) LIBRARY: no
                ( B ) CLONE:

( v i i i ) POSITION IN GENOME:
                ( A ) CHROMOSOME/SEGMENT:
                ( B ) MAP POSITION:
                ( C ) UNITS:

( i x ) FEATURE:
                ( A ) NAME/KEY: upper strand capable of forming a heteroduplex
                        with SEQ ID 18 (het in Fig. 3)
                ( B ) LOCATION:
                ( C ) IDENTIFICATION METHOD: cDNA sequencing
                ( D ) OTHER INFORMATION:

( x ) PUBLICATION INFORMATION:

(A) AUTHORS: Nagy, P.D.
                Bujarski, J.J.
(B) TITLE:Targeting the site of RNA- RNA recombination in virus
        with antisense sequences
(C) JOURNAL: Proc. Natl. Acad. Sci. USA
(D) VOLUME: 90
(E) ISSUE:
(F) PAGES: 6390-6394
(G) DATE: July 1993
(H) DOCUMENT NUMBER:
(I) FILING DATE:
(J) PUBLICATION DATE: July 1993
(K) RELEVANT RESIDUES IN SEQ ID NO: 62

(x i) SEQUENCE DESCRIPTION: SEQ ID NO:17:

CCCUGCUCGG AGGACUAGUC UCGAGGUCUC ACAGGAUCCA GACAAGCGCA UCACUUAACA    60

CAAUUAAAGA UCAAAUCACC AGCGACU    87

(2) INFORMATION FOR SEQ ID NO:18:

(i) SEQUENCE CHARACTERISTICS:
        (A) LENGTH: 78 bases
        (B) TYPE: nucleic
        (C) STRANDEDNESS: single
        (D) TOPOLOGY: linear (i i) MOLECULE TYPE: viral RNA
        (A) DESCRIPTION: BMV RNA1 (wt)

(i i i) HYPOTHETICAL: no (i v) ANTI-SENSE:

(v) FRAGMENT TYPE:

(v i) ORIGINAL SOURCE:
        (A) ORGANISM: brome mosaic virus
        (B) STRAIN: Madison
        (C) INDIVIDUAL ISOLATE: M1
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(v i i) IMMEDIATE SOURCE:
        (A) LIBRARY: no
        (B) CLONE:

(v i i i) POSITION IN GENOME:
        (A) CHROMOSOME/SEGMENT:
        (B) MAP POSITION: BMV RNA1
        (C) UNITS:

(i x) FEATURE:
        (A) NAME/KEY:lower strand capable of forming a heteroduplex
                with SEQ ID 17 (het in Fig. 3)
        (B) LOCATION:
        (C) IDENTIFICATION METHOD: cDNA sequencing
        (D) OTHER INFORMATION:

(x) PUBLICATION INFORMATION:
        (A) AUTHORS: Nagy, P.D.
                Bujarski, J.J.
        (B) TITLE:Targeting the site of RNA- RNA recombination in virus
                with antisense sequences
        (C) JOURNAL: Proc. Natl. Acad. Sci. USA
        (D) VOLUME: 90
        (E) ISSUE:
        (F) PAGES: 6390-6394
        (G) DATE: July 1993
        (H) DOCUMENT NUMBER:
        (I) FILING DATE:
        (J) PUBLICATION DATE: July 1993
        (K) RELEVANT RESIDUES IN SEQ ID NO: 62

( x i ) SEQUENCE DESCRIPTION: SEQ ID NO:18:

GCUCGCUGGU GAUUUGAUCU UUAAUUGUGU UAAGUGAUGC GCUUGUCUCU GUGUGAGACC  60

UCUGCUCGAG GAGAGCCC  78

( 2 ) INFORMATION FOR SEQ ID NO:19:

( i ) SEQUENCE CHARACTERISTICS:
        ( A ) LENGTH: 92 bases
        ( B ) TYPE: nucleic
        ( C ) STRANDEDNESS: single
        ( D ) TOPOLOGY: linear ( i i ) MOLECULE TYPE: viral RNA
        ( A ) DESCRIPTION: recombinant BMV RNA3

( i i i ) HYPOTHETICAL: yes ( i v ) ANTI-SENSE: yes ( v ) FRAGMENT TYPE:

( v i ) ORIGINAL SOURCE:
        ( A ) ORGANISM: brome mosaic virus
        ( B ) STRAIN: Madison
        ( C ) INDIVIDUAL ISOLATE: M1
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY: no
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY: upper strand capable of forming a heteroduplex
            with SEQ ID 20 (het in Fig. 3)
        ( B ) LOCATION:
        ( C ) IDENTIFICATION METHOD: cDNA sequencing
        ( D ) OTHER INFORMATION:

( x ) PUBLICATION INFORMATION:
        ( A ) AUTHORS: Nagy, P.D.
            Bujarski, J.J.
        ( B ) TITLE:Targeting the site of RNA- RNA recombination in virus
            with antisense sequences
        ( C ) JOURNAL: Proc. Natl. Acad. Sci. USA
        ( D ) VOLUME: 90
        ( E ) ISSUE:
        ( F ) PAGES: 6390-6394
        ( G ) DATE: July 1993
        ( H ) DOCUMENT NUMBER:
        ( I ) FILING DATE:
        ( J ) PUBLICATION DATE: July 1993
        ( K ) RELEVANT RESIDUES IN SEQ ID NO: 67

( x i ) SEQUENCE DESCRIPTION: SEQ ID NO:19:

CCCUGCUCGG AGGACUAGUC UCGAGGUCUC ACAGGAUCCA GACAAGCGAC GCGUACUUAA  60

CACGCUAGCU AAAGAUCAAA UCACCAGCGA CU  92

( 2 ) INFORMATION FOR SEQ ID NO:20:

( i ) SEQUENCE CHARACTERISTICS:
        ( A ) LENGTH: 78 bases
        ( B ) TYPE: nucleic
        ( C ) STRANDEDNESS: single
        ( D ) TOPOLOGY: linear ( i i ) MOLECULE TYPE: viral RNA
                     ( A ) DESCRIPTION: BMV RNA1 (wt)

( i i i ) HYPOTHETICAL: no ( i v ) ANTI-SENSE:

( v ) FRAGMENT TYPE:

( v i ) ORIGINAL SOURCE:
                     ( A ) ORGANISM: brome mosaic virus
                     ( B ) STRAIN: Madison
                     ( C ) INDIVIDUAL ISOLATE: M1
                     ( D ) DEVELOPMENTAL STAGE:
                     ( E ) HAPLOTYPE:
                     ( F ) TISSUE TYPE:
                     ( G ) CELL TYPE:
                     ( H ) CELL LINE:
                     ( I ) ORGANELLE:

( v i i ) IMMEDIATE SOURCE:
                     ( A ) LIBRARY: no
                     ( B ) CLONE:

( v i i i ) POSITION IN GENOME:
                     ( A ) CHROMOSOME/SEGMENT:
                     ( B ) MAP POSITION: BMV RNA1
                     ( C ) UNITS:

( i x ) FEATURE:
                     ( A ) NAME/KEY:lower strand capable of forming a heteroduplex
                           with SEQ ID 19 (het in Fig. 3)
                     ( B ) LOCATION: BMV RNA1/BMV RNA3
                     ( C ) IDENTIFICATION METHOD: cDNA sequencing
                     ( D ) OTHER INFORMATION:

( x ) PUBLICATION INFORMATION:
                     ( A ) AUTHORS: Nagy, P.D.
                                    Bujarski, J.J.
                     ( B ) TITLE:Targeting the site of RNA- RNA recombination in virus
                           with antisense sequences
                     ( C ) JOURNAL: Proc. Natl. Acad. Sci. USA
                     ( D ) VOLUME: 90
                     ( E ) ISSUE:
                     ( F ) PAGES: 6390-6394
                     ( G ) DATE: July 1993
                     ( H ) DOCUMENT NUMBER:
                     ( I ) FILING DATE:
                     ( J ) PUBLICATION DATE: July 1993
                     ( K ) RELEVANT RESIDUES IN SEQ ID NO: 67

( x i ) SEQUENCE DESCRIPTION: SEQ ID NO:20:

GCUCGCUGGU    GAUUUGAUCU    UUAAUUGUGU    UAAGUGAUGC    GCUUGUCUCU    GUGUGAGACC         60

UCUGCUCGAG    GAGAGCCC                                                                   78

( 2 ) INFORMATION FOR SEQ ID NO:21:

( i ) SEQUENCE CHARACTERISTICS:
                     ( A ) LENGTH: 89 bases
                     ( B ) TYPE: nucleic
                     ( C ) STRANDEDNESS: single
                     ( D ) TOPOLOGY: linear ( i i ) MOLECULE TYPE: viral RNA
                     ( A ) DESCRIPTION: recombinant BMV RNA3

( i i i ) HYPOTHETICAL: yes ( i v ) ANTI-SENSE: yes ( v ) FRAGMENT TYPE:

( v i ) ORIGINAL SOURCE:
                     ( A ) ORGANISM: brome mosaic virus
                     ( B ) STRAIN: Madison
                     ( C ) INDIVIDUAL ISOLATE: M1

( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY: no
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY: upper strand capable of forming a heteroduplex
                            with SEQ ID 22 (het in Fig. 3)
                    ( B ) LOCATION:
                    ( C ) IDENTIFICATION METHOD: cDNA sequencing
                    ( D ) OTHER INFORMATION:

( x ) PUBLICATION INFORMATION:
                    ( A ) AUTHORS: Nagy, P.D.
                            Bujarski, J.J.
                    ( B ) TITLE:Targeting the site of RNA- RNA recombination in virus
                            with antisense sequences
                    ( C ) JOURNAL: Proc. Natl. Acad. Sci. USA
                    ( D ) VOLUME: 90
                    ( E ) ISSUE:
                    ( F ) PAGES: 6390-6394
                    ( G ) DATE: July 1993
                    ( H ) DOCUMENT NUMBER:
                    ( I ) FILING DATE:
                    ( J ) PUBLICATION DATE: July 1993
                    ( K ) RELEVANT RESIDUES IN SEQ ID NO: 64

( x i ) SEQUENCE DESCRIPTION: SEQ ID NO:21:

CCCUGCUCGG  AGGACUAGUC  UCGAGCAGAG  GUCUCACACA  GAGACAAGCG  CAUCACUUAA         60

CACAAUUAAA  GAUCAAAUCA  CCAGCGACU                                              89

( 2 ) INFORMATION FOR SEQ ID NO:22:

( i ) SEQUENCE CHARACTERISTICS:
                    ( A ) LENGTH: 113 bases
                    ( B ) TYPE: nucleic
                    ( C ) STRANDEDNESS: single
                    ( D ) TOPOLOGY: linear ( i i ) MOLECULE TYPE: viral RNA
                    ( A ) DESCRIPTION: BMV RNA1 (wt)

( i i i ) HYPOTHETICAL: no ( i v ) ANTI-SENSE:

( v ) FRAGMENT TYPE:

( v i ) ORIGINAL SOURCE:
                    ( A ) ORGANISM: brome mosaic virus
                    ( B ) STRAIN: Madison
                    ( C ) INDIVIDUAL ISOLATE: M1
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY: no
                    ( B ) CLONE:

( v i i i ) POSITION IN GENOME:
                    ( A ) CHROMOSOME/SEGMENT:
                    ( B ) MAP POSITION: BMV RNA1

(C) UNITS:

(ix) FEATURE:
    (A) NAME/KEY: lower strand capable of forming a heteroduplex
        with SEQ ID 21 (het in Fig. 3)
    (B) LOCATION: BMV RNA1/BMV RNA3
    (C) IDENTIFICATION METHOD: cDNA sequencing
    (D) OTHER INFORMATION:

(x) PUBLICATION INFORMATION:
    (A) AUTHORS: Nagy, P.D.
        Bujarski, J.J.
    (B) TITLE:Targeting the site of RNA- RNA recombination in virus
        with antisense sequences
    (C) JOURNAL: Proc. Natl. Acad. Sci. USA
    (D) VOLUME: 90
    (E) ISSUE:
    (F) PAGES: 6390-6394
    (G) DATE: July 1993
    (H) DOCUMENT NUMBER:
    (I) FILING DATE:
    (J) PUBLICATION DATE: July 1993
    (K) RELEVANT RESIDUES IN SEQ ID NO: 64

(xi) SEQUENCE DESCRIPTION: SEQ ID NO:22:

| | | | | | | |
|---|---|---|---|---|---|---|
| GCUCGCUGGU | GAUUUGAUCU | UUAAUUGUGU | UAAGUGAUGC | GCUUGUCUCU | GUGUGAGACC | 60 |
| UCUGCUCGAG | GAGAGCCCUG | UUCCAGGUAG | GAACGUUGUG | GUCUAACUCA | GAC | 113 |

(2) INFORMATION FOR SEQ ID NO: 23:

(i) SEQUENCE CHARACTERISTICS:
    (A) LENGTH: 33 bases
    (B) TYPE: nucleic acid
    (C) STRANDEDNESS: single
    (D) TOPOLOGY: linear (ii) MOLECULE TYPE:
    (A) DESCRIPTION: primer (iii) HYPOTHETICAL: yes (iv) ANTI-SENSE: yes (v) FRAGMENT TYPE:

(vi) ORIGINAL SOURCE: synthetic oligonucleotide
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY: primer 2
    (B) LOCATION: 2095 to 2117 on BMV RNA3
    (C) IDENTIFICATION METHOD: synthesized by an oligonucleotide
        synthesizer
    (D) OTHER INFORMATION:

(x) PUBLICATION INFORMATION:
    (A) AUTHORS: Nagy, P. D.
        Bujarski, J. J.
    (B) TITLE: Targeting the site of RNA-RNA recombination in
        brome mosaic virus with antisense sequences ( C ) JOURNAL: Proc. Natl. Acad. Sic. USA
                    ( D ) VOLUME: 90
                    ( E ) ISSUE:
                    ( F ) PAGES: 6390-6394
                    ( G ) DATE: July 1993
                    ( H ) DOCUMENT NUMBER:
                    ( I ) FILING DATE:
                    ( J ) PUBLICATION DATE: July 1993
                    ( K ) RELEVANT RESIDUES IN SEQ ID NO:

( x i ) SEQUENCE DESCRIPTION: SEQ ID NO:23:

CAGTGAATTC TGGTCTCTTT TAGAGATTTA CAG                                     3 3

( 2 ) INFORMATION FOR SEQ ID NO:24:

( i ) SEQUENCE CHARACTERISTICS:
                    ( A ) LENGTH: 26 bases
                    ( B ) TYPE: nucleic acid
                    ( C ) STRANDEDNESS: single
                    ( D ) TOPOLOGY: linear ( i i ) MOLECULE TYPE:
                    ( A ) DESCRIPTION: primer ( i i i ) HYPOTHETICAL: yes ( i v ) ANTI-SENSE: yes ( v ) FRAGMENT TYPE:

( v i ) ORIGINAL SOURCE: synthetic oligonucleotide
                    ( A ) ORGANISM:
                    ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY: primer 2
                    ( B ) LOCATION: 1726 to 1751 on BMV RNA3
                    ( C ) IDENTIFICATION METHOD: synthesized by an oligonucleotide
                          synthesizer
                    ( D ) OTHER INFORMATION:

( x ) PUBLICATION INFORMATION:
                    ( A ) AUTHORS: Nagy, P. D.
                          Bujarski, J. J.
                    ( B ) TITLE: Targeting the site of RNA-RNA recombination in
                          brome mosaic virus with antisense sequences
                    ( C ) JOURNAL: Proc. Natl. Acad. Sic. USA
                    ( D ) VOLUME: 90
                    ( E ) ISSUE:
                    ( F ) PAGES: 6390-6394
                    ( G ) DATE: July 1993
                    ( H ) DOCUMENT NUMBER:
                    ( I ) FILING DATE:
                    ( J ) PUBLICATION DATE: July 1993
                    ( K ) RELEVANT RESIDUES IN SEQ ID NO:

( x i ) SEQUENCE DESCRIPTION: SEQ ID NO:24:

CTGAAGCAGT GCCTGCTAAG GCGGTC                                             2 6

( 2 ) INFORMATION FOR SEQ ID NO:25:

(i) SEQUENCE CHARACTERISTICS:
  (A) LENGTH: 33 bases
  (B) TYPE: nucleic acid
  (C) STRANDEDNESS: single
  (D) TOPOLOGY: linear (ii) MOLECULE TYPE:
  (A) DESCRIPTION: primer (iii) HYPOTHETICAL: yes (iv) ANTI-SENSE: yes (v) FRAGMENT TYPE:

(vi) ORIGINAL SOURCE: synthetic oligonucleotide
  (A) ORGANISM:
  (B) STRAIN:
  (C) INDIVIDUAL ISOLATE:
  (D) DEVELOPMENTAL STAGE:
  (E) HAPLOTYPE:
  (F) TISSUE TYPE:
  (G) CELL TYPE:
  (H) CELL LINE:
  (I) ORGANELLE:

(vii) IMMEDIATE SOURCE:
  (A) LIBRARY:
  (B) CLONE:

(viii) POSITION IN GENOME:
  (A) CHROMOSOME/SEGMENT:
  (B) MAP POSITION:
  (C) UNITS:

(ix) FEATURE:
  (A) NAME/KEY: primer 3
  (B) LOCATION: 2127 TO 2150 on BMV RNA3
  (C) IDENTIFICATION METHOD: synthesized by an oligonucleotide synthesizer
  (D) OTHER INFORMATION:

(x) PUBLICATION INFORMATION:
  (A) AUTHORS: Nagy, P. D.
    Bujarski, J. J.
  (B) TITLE: Targeting the site of RNA-RNA recombination in brome mosaic virus with antisense sequences
  (C) JOURNAL: Proc. Natl. Acad. Sic. USA
  (D) VOLUME: 90
  (E) ISSUE:
  (F) PAGES: 6390-6394
  (G) DATE: July 1993
  (H) DOCUMENT NUMBER:
  (I) FILING DATE:
  (J) PUBLICATION DATE: July 1993
  (K) RELEVANT RESIDUES IN SEQ ID NO:

(xi) SEQUENCE DESCRIPTION: SEQ ID NO:25:

CAGTGAATTC TTTCGACTAG GCGCTGCCCA CCA                33

(2) INFORMATION FOR SEQ ID NO:26:

(i) SEQUENCE CHARACTERISTICS:
  (A) LENGTH: 30 bases
  (B) TYPE: nucleic acid
  (C) STRANDEDNESS: single
  (D) TOPOLOGY: linear (ii) MOLECULE TYPE:
  (A) DESCRIPTION: primer (iii) HYPOTHETICAL: yes (iv) ANTI-SENSE: yes (v) FRAGMENT TYPE:

(vi) ORIGINAL SOURCE: synthetic oligonucleotide
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY: primer 4
    (B) LOCATION: 2853 TO 2992 on BMV RNA3
    (C) IDENTIFICATION METHOD: synthesized by an oligonucleotide
         synthesizer
    (D) OTHER INFORMATION:

(x) PUBLICATION INFORMATION:
    (A) AUTHORS: Nagy, P. D.
                 Bujarski, J. J.
    (B) TITLE: Targeting the site of RNA-RNA recombination in
         brome mosaic virus with antisense sequences
    (C) JOURNAL: Proc. Natl. Acad. Sic. USA
    (D) VOLUME: 90
    (E) ISSUE:
    (F) PAGES: 6390-6394
    (G) DATE: July 1993
    (H) DOCUMENT NUMBER:
    (I) FILING DATE:
    (J) PUBLICATION DATE: July 1993
    (K) RELEVANT RESIDUES IN SEQ ID NO:

(xi) SEQUENCE DESCRIPTION: SEQ ID NO:26:

CAGTACTAGT TTAAGTGATG CGCTTGTCTC                              30

(2) INFORMATION FOR SEQ ID NO:27:

(i) SEQUENCE CHARACTERISTICS:
        (A) LENGTH: 31 bases
        (B) TYPE: nucleic acid
        (C) STRANDEDNESS: single
        (D) TOPOLOGY: linear (ii) MOLECULE TYPE:
        (A) DESCRIPTION: primer (iii) HYPOTHETICAL: yes (iv) ANTI-SENSE: yes (v) FRAGMENT TYPE:

(vi) ORIGINAL SOURCE: synthetic oligonucleotide
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:

( A ) CHROMOSOME/SEGMENT:
( B ) MAP POSITION:
( C ) UNITS:

( i x ) FEATURE:
( A ) NAME/KEY: primer 5
( B ) LOCATION: 2853 TO 2992 on BMV RNA3
( C ) IDENTIFICATION METHOD: synthesized by an oligonucleotide
synthesizer
( D ) OTHER INFORMATION:

( x ) PUBLICATION INFORMATION:
( A ) AUTHORS: Nagy, P. D.
Bujarski, J. J.
( B ) TITLE: Targeting the site of RNA-RNA recombination in
brome mosaic virus with antisense sequences
( C ) JOURNAL: Proc. Natl. Acad. Sic. USA
( D ) VOLUME: 90
( E ) ISSUE:
( F ) PAGES: 6390-6394
( G ) DATE: July 1993
( H ) DOCUMENT NUMBER:
( I ) FILING DATE:
( J ) PUBLICATION DATE: July 1993
( K ) RELEVANT RESIDUES IN SEQ ID NO:

( x i ) SEQUENCE DESCRIPTION: SEQ ID NO:27:

CAGTACTAGT CGCTTGTCTC TGTGTGAGAC C    31

( 2 ) INFORMATION FOR SEQ ID NO:28:

( i ) SEQUENCE CHARACTERISTICS:
( A ) LENGTH: 30 bases
( B ) TYPE: nucleic acid
( C ) STRANDEDNESS: single
( D ) TOPOLOGY: linear ( i i ) MOLECULE TYPE:
( A ) DESCRIPTION: primer ( i i i ) HYPOTHETICAL: yes ( i v ) ANTI-SENSE: yes ( v ) FRAGMENT TYPE:

( v i ) ORIGINAL SOURCE: synthetic oligonucleotide
( A ) ORGANISM:
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( v i i ) IMMEDIATE SOURCE:
( A ) LIBRARY:
( B ) CLONE:

( v i i i ) POSITION IN GENOME:
( A ) CHROMOSOME/SEGMENT:
( B ) MAP POSITION:
( C ) UNITS:

( i x ) FEATURE:
( A ) NAME/KEY: primer 6
( B ) LOCATION: 2853 TO 2992 on BMV RNA3
( C ) IDENTIFICATION METHOD: synthesized by an oligonucleotide
synthesizer
( D ) OTHER INFORMATION:

( x ) PUBLICATION INFORMATION:
( A ) AUTHORS: Nagy, P. D.
Bujarski, J. J.
( B ) TITLE: Targeting the site of RNA-RNA recombination in
brome mosaic virus with antisense sequences (C) JOURNAL: Proc. Natl. Acad. Sic. USA
(D) VOLUME: 90
(E) ISSUE:
(F) PAGES: 6390-6394
(G) DATE: July 1993
(H) DOCUMENT NUMBER:
(I) FILING DATE:
(J) PUBLICATION DATE: July 1993
(K) RELEVANT RESIDUES IN SEQ ID NO: 30

(xi) SEQUENCE DESCRIPTION: SEQ ID NO:28:

CAGTACTAGT TGTGTGAGAC CTCTGCTCGA 30

(2) INFORMATION FOR SEQ ID NO:29:

(i) SEQUENCE CHARACTERISTICS:
(A) LENGTH: 40 bases
(B) TYPE: nucleic acid
(C) STRANDEDNESS: single
(D) TOPOLOGY: linear (ii) MOLECULE TYPE:
(A) DESCRIPTION: primer (iii) HYPOTHETICAL: yes (iv) ANTI-SENSE: yes (v) FRAGMENT TYPE:

(vi) ORIGINAL SOURCE: synthetic oligonucleotide
(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY: primer 7
(B) LOCATION: 2853 TO 2992 on BMV RNA3
(C) IDENTIFICATION METHOD: synthesized by an oligonucleotide
    synthesizer
(D) OTHER INFORMATION:

(x) PUBLICATION INFORMATION:
(A) AUTHORS: Nagy, P. D.
    Bujarski, J. J.
(B) TITLE: Targeting the site of RNA-RNA recombination in
    brome mosaic virus with antisense sequences
(C) JOURNAL: Proc. Natl. Acad. Sic. USA
(D) VOLUME: 90
(E) ISSUE:
(F) PAGES: 6390-6394
(G) DATE: July 1993
(H) DOCUMENT NUMBER:
(I) FILING DATE:
(J) PUBLICATION DATE: July 1993
(K) RELEVANT RESIDUES IN SEQ ID NO: 40

(xi) SEQUENCE DESCRIPTION: SEQ ID NO:29:

TAGTCTCGAG CAGAGGTTTT ATATAGAGACA AGCGCATCA 40

(2) INFORMATION FOR SEQ ID NO:30:

(i) SEQUENCE CHARACTERISTICS:
    (A) LENGTH: 47 bases
    (B) TYPE: nucleic acid
    (C) STRANDEDNESS: single
    (D) TOPOLOGY: linear (ii) MOLECULE TYPE:
    (A) DESCRIPTION: primer (iii) HYPOTHETICAL: yes (iv) ANTI-SENSE: yes (v) FRAGMENT TYPE:

(vi) ORIGINAL SOURCE: synthetic oligonucleotide
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY: primer 8
    (B) LOCATION: 2853 TO 2992 on BMV RNA3
    (C) IDENTIFICATION METHOD: synthesized by an oligonucleotide
        synthesizer
    (D) OTHER INFORMATION:

(x) PUBLICATION INFORMATION:
    (A) AUTHORS: Nagy, P. D.
        Bujarski, J. J.
    (B) TITLE: Targeting the site of RNA-RNA recombination in
        brome mosaic virus with antisense sequences
    (C) JOURNAL: Proc. Natl. Acad. Sic. USA
    (D) VOLUME: 90
    (E) ISSUE:
    (F) PAGES: 6390-6394
    (G) DATE: July 1993
    (H) DOCUMENT NUMBER:
    (I) FILING DATE:
    (J) PUBLICATION DATE: July 1993
    (K) RELEVANT RESIDUES IN SEQ ID NO: 47

(xi) SEQUENCE DESCRIPTION: SEQ ID NO:30:

```
CTAGTCTCGA GGTCTCACAG GATCCAGACA AGCGCATCCC TTAACAC        47
```

(2) INFORMATION FOR SEQ ID NO:31:

(i) SEQUENCE CHARACTERISTICS:
    (A) LENGTH: 57 bases
    (B) TYPE: nucleic acid
    (C) STRANDEDNESS: single
    (D) TOPOLOGY: linear (ii) MOLECULE TYPE:
    (A) DESCRIPTION: primer (iii) HYPOTHETICAL: yes (iv) ANTI-SENSE: yes (v) FRAGMENT TYPE:

```
( v i ) ORIGINAL SOURCE: synthetic oligonucleotide
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY: primer 9
        ( B ) LOCATION: 2853 TO 2992 on BMV RNA3
        ( C ) IDENTIFICATION METHOD: synthesized by an oligonucleotide
              synthesizer
        ( D ) OTHER INFORMATION:

( x ) PUBLICATION INFORMATION:
        ( A ) AUTHORS: Nagy, P. D.
                      Bujarski, J. J.
        ( B ) TITLE: Targeting the site of RNA-RNA recombination in
              brome mosaic virus with antisense sequences
        ( C ) JOURNAL: Proc. Natl. Acad. Sic. USA
        ( D ) VOLUME: 90
        ( E ) ISSUE:
        ( F ) PAGES: 6390-6394
        ( G ) DATE: July 1993
        ( H ) DOCUMENT NUMBER:
        ( I ) FILING DATE:
        ( J ) PUBLICATION DATE: July 1993
        ( K ) RELEVANT RESIDUES IN SEQ ID NO: 57

( x i ) SEQUENCE DESCRIPTION: SEQ ID NO:31:

ACAGGATCCA  GACAAGCGAC  GCGTACTTAA  CACGCTAGCT  AAAGATCAAA  TCACCAG                57
```